(12) United States Patent
Tsuzuki et al.

(10) Patent No.: US 8,682,608 B2
(45) Date of Patent: Mar. 25, 2014

(54) BEHAVIOR RECOGNITION APPARATUS

(75) Inventors: Takashi Tsuzuki, Osaka (JP); Mototaka Yoshioka, Osaka (JP); Kazutoyo Takata, Osaka (JP)

(73) Assignee: Panasonic Corporation, Osaka (JP)

( * ) Notice: Subject to any disclaimer, the term of this patent is extended or adjusted under 35 U.S.C. 154(b) by 325 days.

(21) Appl. No.: 13/058,072

(22) PCT Filed: May 27, 2010

(86) PCT No.: PCT/JP2010/003556
§ 371 (c)(1),
(2), (4) Date: Feb. 8, 2011

(87) PCT Pub. No.: WO2010/137325
PCT Pub. Date: Dec. 2, 2010

(65) Prior Publication Data
US 2011/0144543 A1    Jun. 16, 2011

(30) Foreign Application Priority Data
May 27, 2009 (JP) .................................. 2009-128314

(51) Int. Cl.
*G01P 15/00* (2006.01)
(52) U.S. Cl.
USPC ......................................... 702/141; 600/595
(58) Field of Classification Search
USPC ......................................... 702/141; 600/595
See application file for complete search history.

(56) References Cited

U.S. PATENT DOCUMENTS

| 5,699,441 | A | 12/1997 | Sagawa et al. |
| 5,887,069 | A | 3/1999 | Sakou et al. |
| 6,183,365 | B1 | 2/2001 | Tonomura et al. |
| 6,571,193 | B1 | 5/2003 | Unuma et al. |
| 2003/0208335 | A1 | 11/2003 | Unuma et al. |

(Continued)

FOREIGN PATENT DOCUMENTS

| CN | 1194691 | 9/1998 |
| CN | 1285504 | 2/2001 |

(Continued)

OTHER PUBLICATIONS

International Search Report issued Aug. 10, 2010 in corresponding International Application No. PCT/JP2010/003556.

(Continued)

*Primary Examiner* — Max Hindenburg
*Assistant Examiner* — Renee Danega
(74) *Attorney, Agent, or Firm* — Wenderoth, Lind & Ponack, L.L.P.

(57) ABSTRACT

A behavior recognition apparatus includes a hand movement observation unit which outputs hand movement data indicating a hand movement made by a user; a velocity variation detection unit which detects a time at which the hand movement matches a predetermined movement pattern; and a feature selection unit which selects the hand movement data outputted at the time detected by the velocity variation detection unit. A standard behavior pattern storage unit stores a movement pattern data sequence represented by a hand movement data sequence, in association with a user behavior; and a behavior recognition unit calculates a degree of similarity between the movement pattern data sequence stored in the standard behavior pattern storage unit and the hand movement data selected by the feature selection unit, and recognizes, as the user behavior, a behavior represented by the movement pattern data sequence when the degree of similarity is the highest.

13 Claims, 19 Drawing Sheets

(56) References Cited

U.S. PATENT DOCUMENTS

2007/0159455 A1    7/2007   Lin
2008/0192005 A1*   8/2008   Elgoyhen et al. .............. 345/158
2010/0199230 A1*   8/2010   Latta et al. .................... 715/863

FOREIGN PATENT DOCUMENTS

| | | |
|---|---|---|
| JP | 6-66701 | 3/1994 |
| JP | 6-67601 | 3/1994 |
| JP | 10-113343 | 5/1998 |
| JP | 2000-213967 | 8/2000 |
| JP | 2007-187555 | 7/2007 |

OTHER PUBLICATIONS

Search Report dated Sep. 12, 2013 in corresponding Chinese Application No. 201080003387.6, with English translation.

* cited by examiner cos θ : Cosine distance

FIG. 9

| Movement pattern data sequence ID | Behavior label | Movement pattern data sequence | Arm posture |
|---|---|---|---|
| 1 | Drink beverage | Acceleration ~~~ →t | Hand: in front of chest or mouth |
| 2 | Eat food | Acceleration ~~~ →t | Hand: in front of chest or mouth |
| 3 | Brush teeth | Acceleration MMMM →t | Hand: in front of mouth |
| ---- | ---- | ---- | ---- |

FIG. 13

| Movement pattern data sequence ID | Behavior label | Movement pattern data sequence | Arm posture | Body posture |
|---|---|---|---|---|
| 1 | Drink beverage | Acceleration | Hand: in front of chest or mouth | Standing position |
| 2 | Eat food | Acceleration | Hand: in front of chest or mouth | Standing position |
| 3 | Brush teeth | Acceleration | Hand: in front of mouth | Standing position |
| ---- | ---- | ---- | ---- | ---- |

FIG. 16

| Movement pattern data sequence ID | Behavior label | Movement pattern data sequence | Grip state |
|---|---|---|---|
| 1 | Drink beverage | Acceleration waveform → t | Grip |
| 2 | Eat food | Acceleration waveform → t | Grip |
| 3 | Brush teeth | Acceleration waveform → t | Grip |
| ---- | ---- | ---- | ---- |

FIG. 19

| Movement pattern data sequence ID | Behavior label | Movement pattern data sequence | Arm posture | Grip state |
|---|---|---|---|---|
| 1 | Drink beverage | Acceleration waveform vs. t | Hand: in front of chest or mouth | Grip |
| 2 | Eat food | Acceleration waveform vs. t | Hand: in front of chest or mouth | Grip |
| 3 | Brush teeth | Acceleration waveform vs. t | Hand: in front of mouth | Grip |
| ---- | ---- | ---- | ---- | ---- |

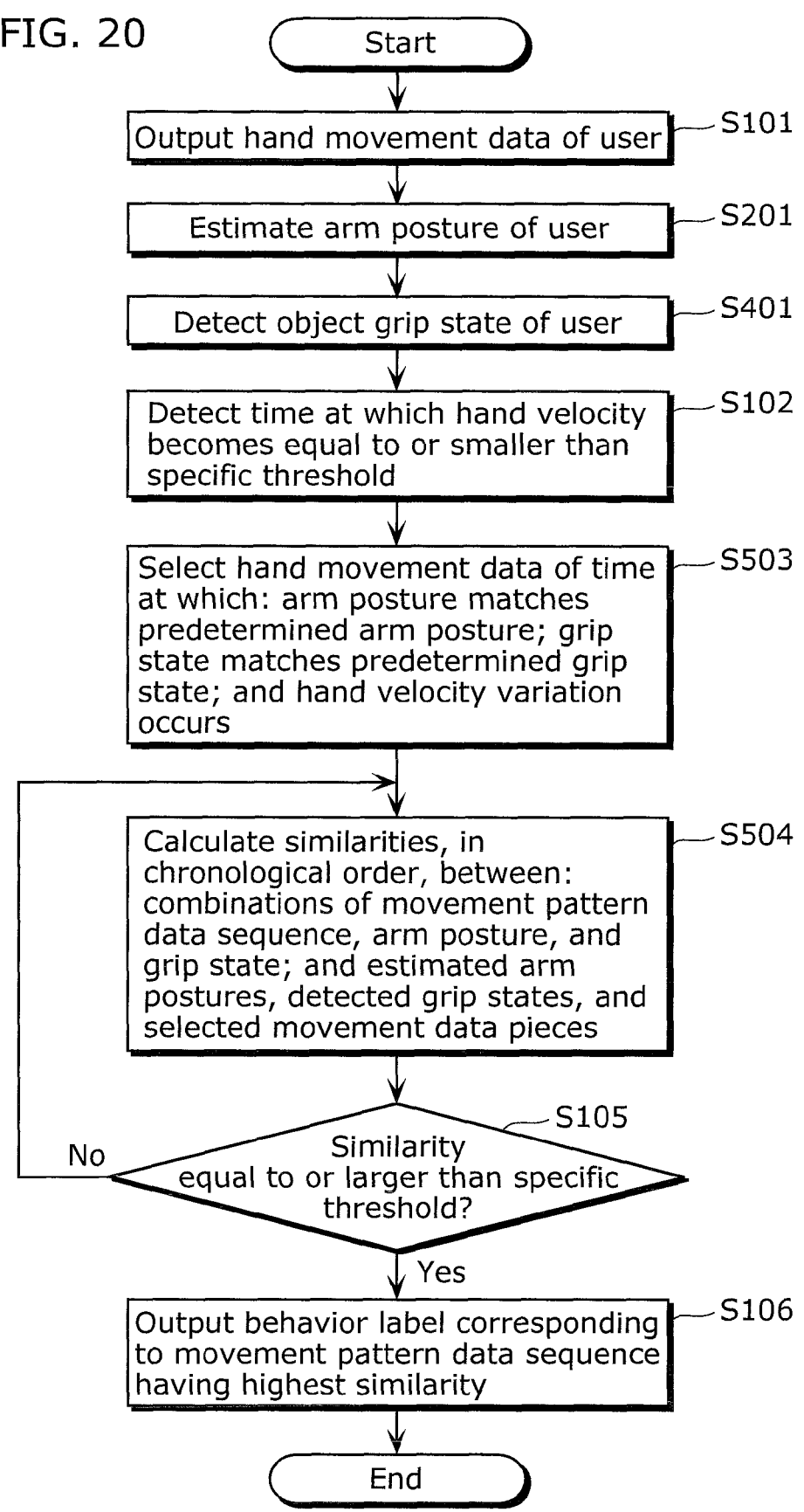

BEHAVIOR RECOGNITION APPARATUS

BACKGROUND OF INVENTION

1. Technical Field

The present invention relates to a behavior recognition apparatus which recognizes a behavior of a user from a hand movement made by the user.

2. Background Art

As a conventional apparatus for recognizing a behavior of a user, a movement recognition system which can recognize a movement of the user from information provided by multiple acceleration sensors set in an environment has been proposed (see Patent Reference 1, for example).

Citation List

Patent Literature

[PTL 1]
Japanese Unexamined Patent Application Publication No. 2007-187555

SUMMARY OF INVENTION

However, the conventional apparatus for recognizing the movement of the user extracts data at predetermined intervals and uses the extracted data for movement recognition. On account of this, recognition needs to be performed in consideration of environmental changes. For example, in the case where the user uses an object in the behavior, a trajectory formed by a hand of the user reaching for the object is different for each environment where the object is placed. However, when the data is uniformly extracted at the predetermined intervals, this means that data corresponding to the hand trajectory is also extracted and ends up being used for movement recognition. For this reason, movement recognition needs to be performed in consideration of all different hand trajectories. That is to say, in order to create a standard pattern for movement recognition taking account of the environmental changes, it is necessary to collect all hand trajectories.

The present invention is conceived in view of the aforementioned problem, and has an object to provide a behavior recognition apparatus which is capable of recognizing, without consideration of environmental changes, a user behavior from data on a hand movement made by a user.

In order to achieve the above object, the behavior recognition apparatus in an aspect of the present invention is a behavior recognition apparatus which recognizes a user behavior from a hand movement made by a user, the behavior recognition apparatus including: a hand movement observation unit which detects the hand movement made by the user and outputs hand movement data indicating the hand movement; a velocity variation detection unit which detects a time at which the hand movement made by the user matches a predetermined movement pattern, from the hand movement data outputted from the hand movement observation unit; a feature selection unit which selects the hand movement data that is outputted from the hand movement observation unit at the time detected by the velocity variation detection unit; a standard behavior pattern storage unit which stores a movement pattern data sequence represented by a hand movement data sequence, in association with the user behavior; and a behavior recognition unit which calculates a degree of similarity between the movement pattern data sequence stored in the standard behavior pattern storage unit and the hand movement data selected by the feature selection unit, and recognizes, as the user behavior, a behavior represented by the movement pattern data sequence when the degree of similarity is highest.

According to this configuration, when a motion trajectory is different each time even in similar kinds of behavior, only a hand movement intentionally made by the user to achieve a behavior, that is, a hand movement characterizing the behavior, can be extracted and processed as a recognition target. Thus, the behavior of the user can be recognized from the data on the hand movement made by the user, without consideration of environmental changes.

It should be noted that the present invention can be implemented not only as a behavior recognition apparatus including the characteristic processing units as described above, but also as a behavior recognition method having, as steps, the characteristic processing units included in the behavior recognition apparatus. Also, the present invention can be implemented as a program causing a computer to execute the characteristic steps including in the behavior recognition method. It should be obvious that such a program can be distributed via a computer-readable recording medium such as a Compact Disc-Read Only Memory (CD-ROM) or via a communication network such as the Internet.

Advantageous Effects of Invention

The present invention can provide a behavior recognition apparatus which is capable of recognizing, without consideration of environmental changes, a user behavior from data on a hand movement made by a user.

BRIEF DESCRIPTION OF DRAWINGS

FIG. 1 is a block diagram showing a configuration of a behavior recognition apparatus in a first embodiment.
FIG. 2 is a diagram showing an example of data stored in a standard behavior pattern storage unit and used by the behavior recognition apparatus in the first embodiment.
FIG. 3 is a flowchart showing an operation performed by the behavior recognition apparatus in the first embodiment.
FIG. 4 is a diagram showing an example of a behavior.
FIG. 5 is a diagram showing an example of variation in hand velocity in the first embodiment.
FIG. 6 is a diagram showing an example of variations in hand acceleration and hand velocity in the first embodiment.
FIG. 7A is a diagram explaining a method of selecting velocity data based on the velocity variation, in the first embodiment.
FIG. 7B is a diagram explaining a cosine distance.
FIG. 8 is a block diagram showing a configuration of a behavior recognition apparatus in a second embodiment.
[FIG. 9]
FIG. 9 is a diagram showing an example of data stored in a standard behavior pattern storage unit and used by the behavior recognition apparatus in the second embodiment.

FIG. 10 is a diagram showing an example of a positional relation between a behavior and a space relative to the user's body, in a second embodiment.

FIG. 11 is a flowchart showing an operation performed by the behavior recognition apparatus in the second embodiment.

FIG. 12 is a block diagram showing a configuration of a behavior recognition apparatus in a third embodiment.

[FIG. 13]

FIG. 13 is a diagram showing an example of data stored in a standard behavior pattern storage unit and used by the behavior recognition apparatus in the third embodiment.

FIG. 14 is a flowchart showing an operation performed by the behavior recognition apparatus in the third embodiment.

FIG. 15 is a block diagram showing a configuration of a behavior recognition apparatus in a fourth embodiment.

[FIG. 16]

FIG. 16 is a diagram showing an example of data stored in a standard behavior pattern storage unit and used by the behavior recognition apparatus in the fourth embodiment.

FIG. 17 is a flowchart showing an operation performed by the behavior recognition apparatus in the fourth embodiment.

FIG. 18 is a block diagram showing a configuration of a behavior recognition apparatus in a fifth embodiment.

[FIG. 19]

FIG. 19 is a diagram showing an example of data stored in a standard behavior pattern storage unit and used by the behavior recognition apparatus in the fifth embodiment.

[FIG. 20]

FIG. 20 is a flowchart showing an operation performed by the behavior recognition apparatus in the fifth embodiment.

DETAILED DESCRIPTION OF INVENTION (First Embodiment)

The following is a description of a behavior recognition apparatus in the first embodiment according to the present invention, with reference to the drawings.

Figure 1:
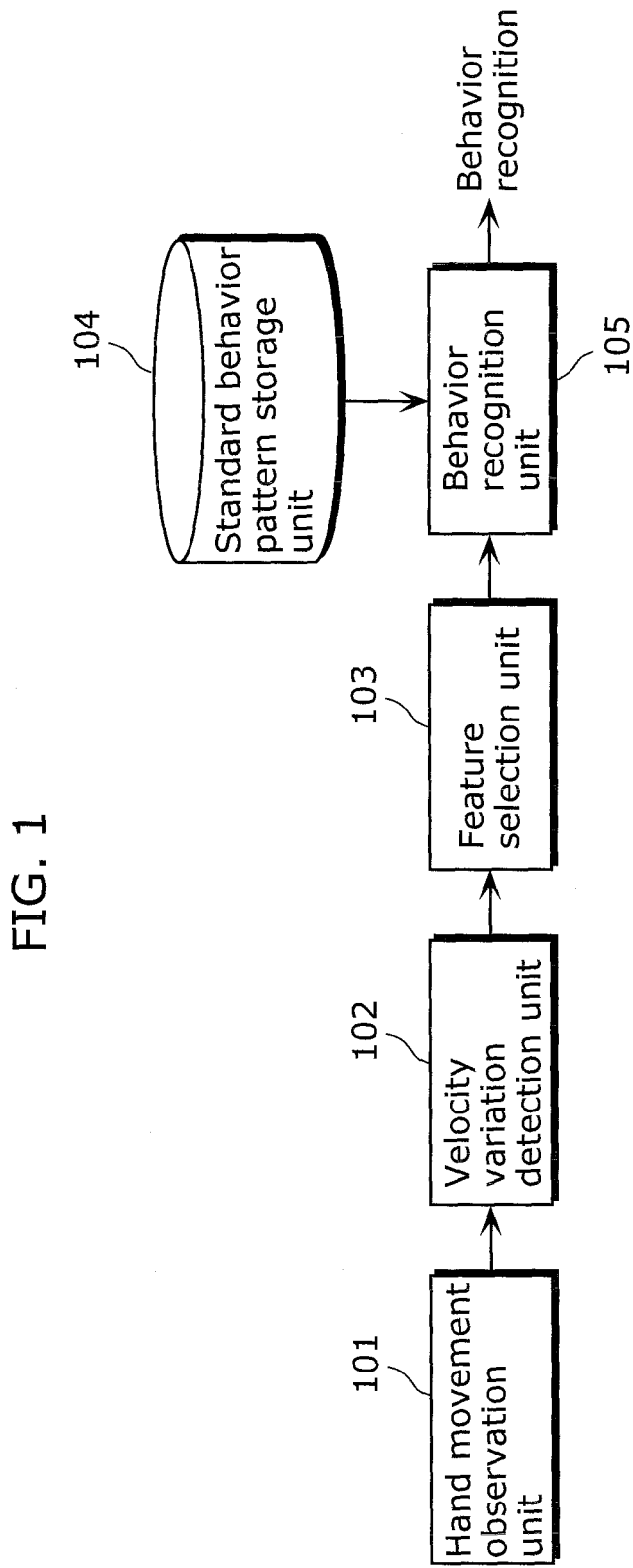
[FIG. 1]

FIG. 1 is a block diagram showing a configuration of the behavior recognition apparatus in the first embodiment.

The behavior recognition apparatus recognizes a user behavior from a hand movement made by a user. The behavior recognition apparatus includes a hand movement observation unit 101, a velocity variation detection unit 102, a feature selection unit 103, a standard behavior pattern storage unit 104, and a behavior recognition unit 105.

The hand movement observation unit 101 detects a hand movement made by the user and outputs hand movement data indicating the hand movement. For example, the hand movement observation unit 101 is configured with an input device, including an acceleration sensor and an angular velocity sensor, which senses a hand movement. Using this input device, the hand movement observation unit 101 outputs the hand movement data that includes acceleration data, angular velocity data, and velocity data in three axes of the hand (that is, X, Y, and Z directions). The hand movement observation unit 101 is worn on the wrist of the user, for example.

The velocity variation detection unit 102 detects a time at which a hand movement of the user matches a predetermined movement pattern, from the hand movement data outputted from the hand movement observation unit 101. It should be noted that, in the following description, a time at which a variation in the hand velocity occurs is detected as the time at which the hand movement of the user matches the predetermined movement pattern.

The feature selection unit 103 selects the hand movement data that is outputted from the hand movement observation unit 101 at the time of occurrence of the hand velocity variation detected by the velocity variation detection unit 102.

Figure 2:
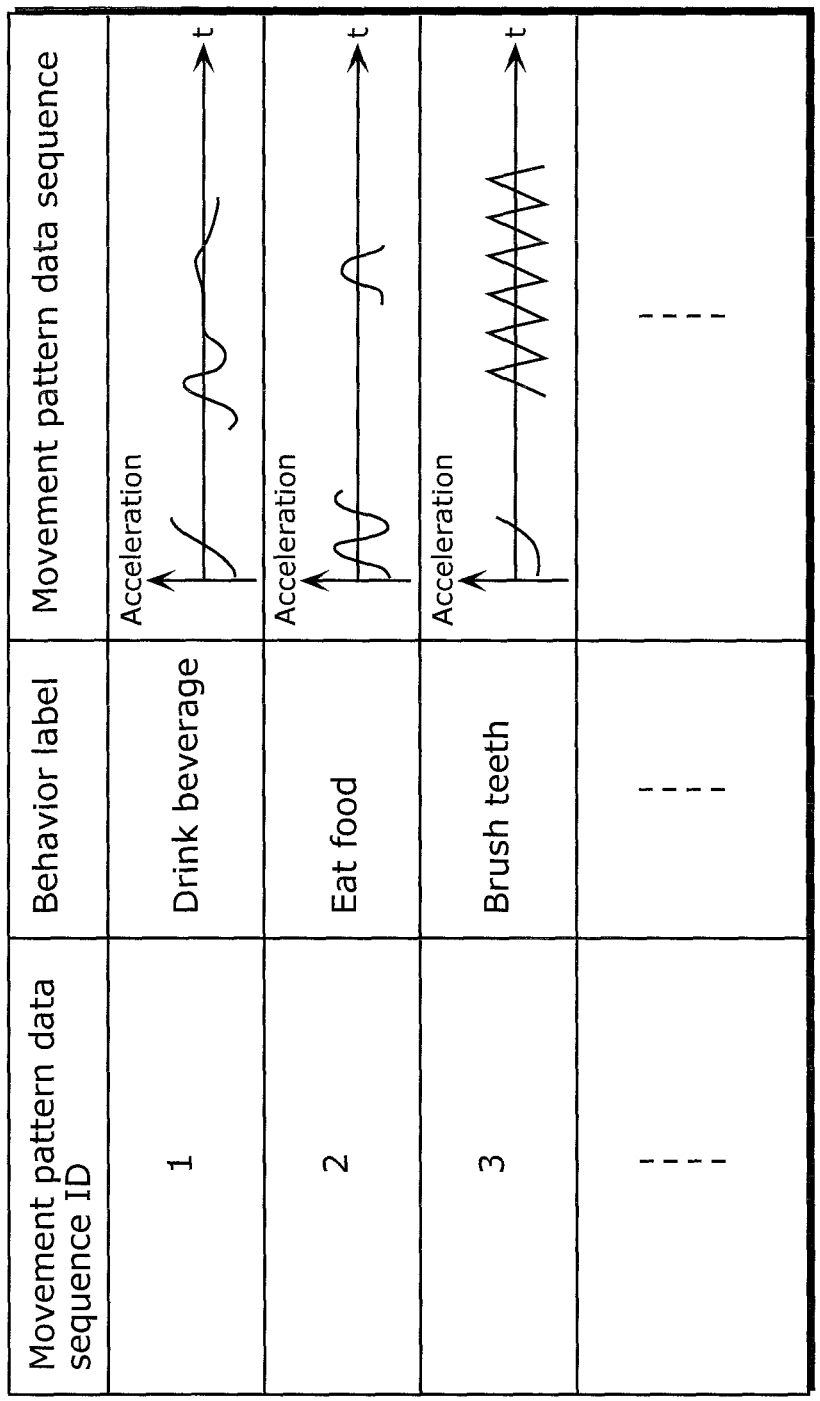
[FIG. 2]

The standard behavior pattern storage unit 104 stores, for each of behaviors of the user, a movement pattern data sequence in which the present behavior is represented by a hand movement data sequence of times at which the variations occur in the hand velocity. FIG. 2 is a diagram showing an example of the data stored in the standard behavior pattern storage unit 104. As shown in FIG. 2, the standard behavior pattern storage unit 104 stores, for each of the behaviors of the user, a movement pattern data sequence ID, a behavior label, and a movement pattern data sequence. The movement pattern data sequence ID is an identifier of the movement pattern data sequence. The behavior label is data indicating the present behavior. In this diagram, a sequence of hand acceleration data of times at which the variations in the hand velocity occur is shown as an example of the movement pattern data sequence. Note that, however, the movement pattern data sequence is not limited to this. For example, the movement pattern data sequence may be a hand velocity data sequence. Alternatively, in the case of behavior recognition using a hidden Markov model (HMM), the movement pattern data sequence may be a HMM parameter sequence. As examples of pairs of the movement pattern data sequence ID and the behavior label, "1" and "Drink beverage", "2" and "Eat food", and "3" and "Brush teeth" are stored. Note that the movement pattern data sequence identified by the movement pattern data sequence ID "1" corresponding to the behavior label "Drink beverage" is obtained by learning, in chronological order, hand movement data of times at which the variations in the hand velocity are large with small environmental changes. Examples of the hand movement data of times at which the variations in the hand velocity are large with small environmental changes include hand movements such as "Hold glass", "Put glass to mouth", "Tilt glass and pour beverage into mouth", and "Put glass down". Also, examples of the times at which the variations in the hand velocity are large with small environment changes include times such as when the user's hand which has been moving stops and when the user's hand moves while changing orientation at a fixed angle or an angle smaller than the fixed angle.

The behavior recognition unit 105 calculates, for each of the movement pattern data sequences stored in the standard behavior pattern storage unit 104, a degree of similarity between the present movement pattern data sequence and the hand movement data selected by the feature selection unit 103. Moreover, the behavior recognition unit 105 outputs the behavior label corresponding to the movement pattern data sequence having the highest degree of similarity. In other words, the behavior recognition unit 105 recognizes the behavior of the user.

Figure 3:
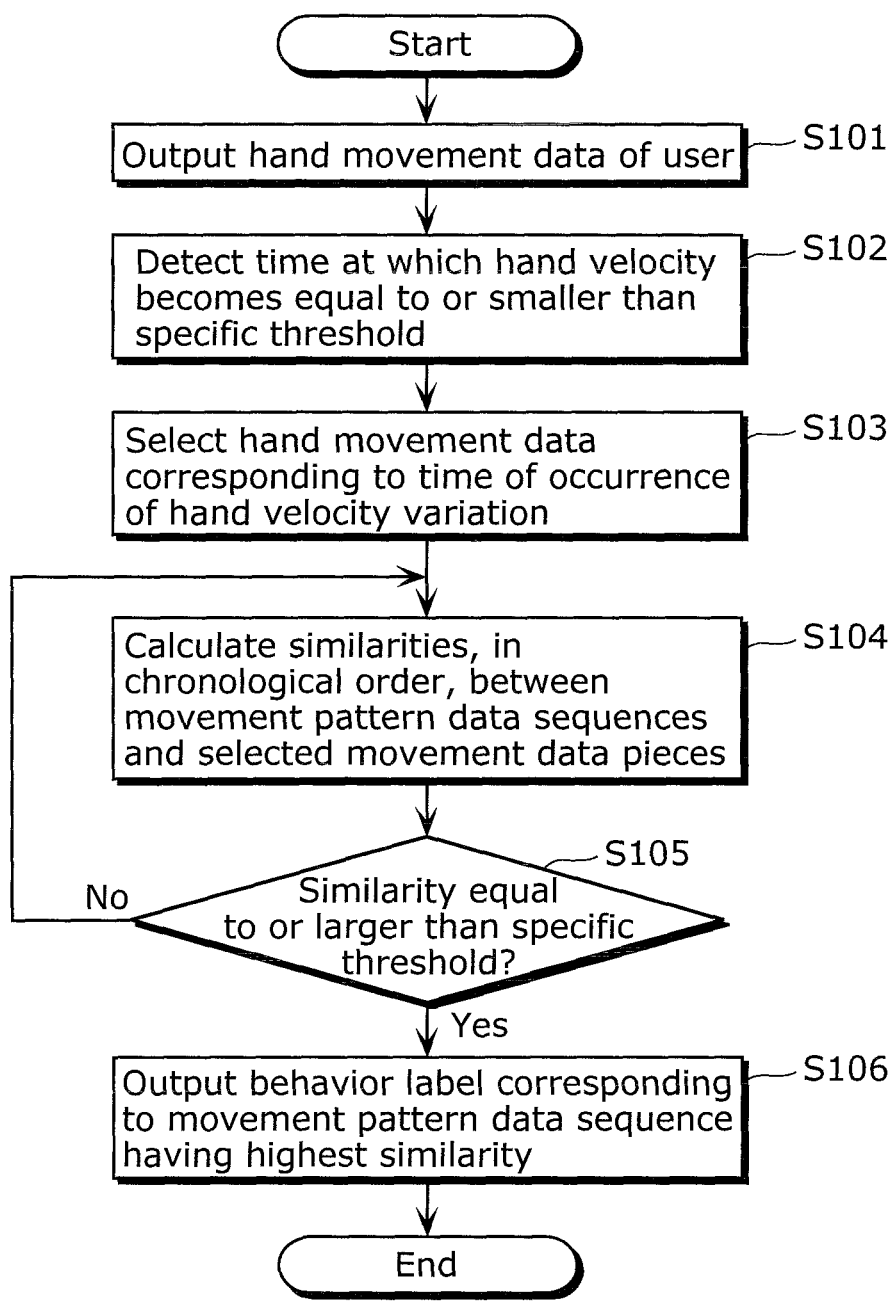
[FIG. 3]

An example of an operation performed by the behavior recognition apparatus configured as described above in the present embodiment is explained as follows, with reference to the block diagram shown in FIG. 1 and a flowchart shown in FIG. 3.

Figure 4:
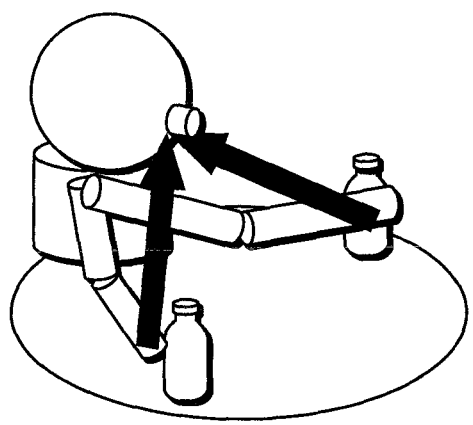
[FIG. 4]

The hand movement observation unit 101 senses a hand movement made by the user and then outputs the hand movement data (i.e., the acceleration data, angular velocity data, and velocity is data of the hand) (step S101). As a specific example of a behavior, suppose that the user lifts a glass of water from the table and drinks the glass of water. The hand movement observation unit 101 outputs the hand movement data (i.e., the acceleration data, angular velocity data, and velocity data of the hand) on this behavior of drinking a beverage. A conceptual drawing of this behavior is shown in FIG. 4. In FIG. 4, the hand movement made during the movement "Hold glass" and the hand movement made during the movement "Put glass to mouth" do not change according to the position of the glass. However, this diagram shows that a trajectory of the hand formed when the user moves the glass from the table to the user's mouth depends on the position of the glass on the table.

Figure 5:
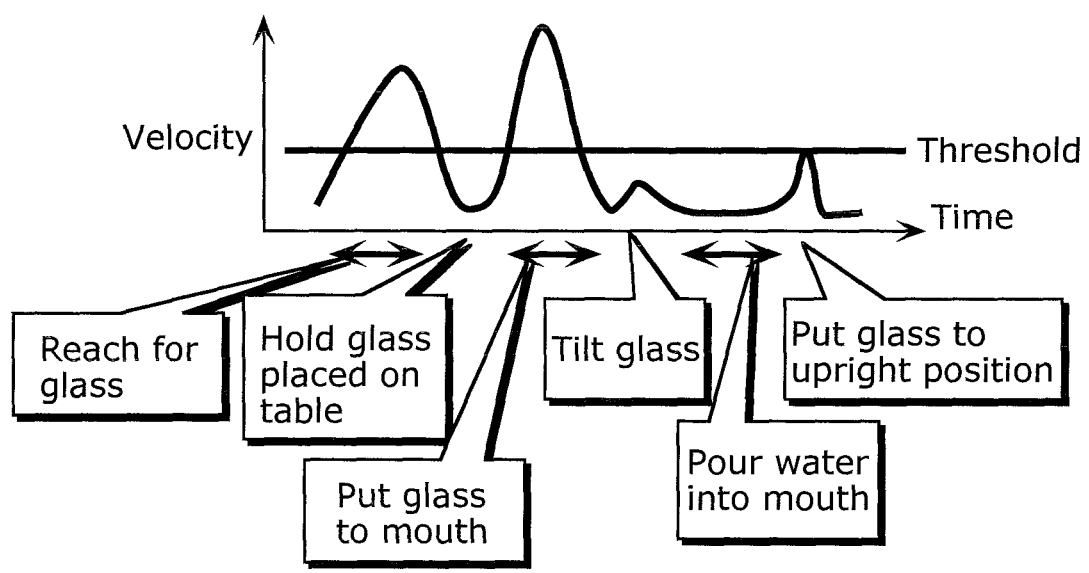
[FIG. 5]

From the hand movement data outputted from the hand movement observation unit 101, the velocity variation detection unit 102 detects a time at which a hand velocity variation occurs, such as a time at which the hand velocity becomes equal to or smaller than a specific threshold (step S102). In the above example, the hand velocity becomes equal to or smaller than the specific threshold at the time when the user holds the glass after moving the hand to reach for the glass. Thus, the velocity variation detection unit 102 detects this time. A conceptual drawing at this time is shown in FIG. 5. In FIG. 5, the hand velocity further becomes equal to or smaller than the specific threshold at each of the times when the user tilts the glass, pours the beverage into the mouth, and puts the glass back to the upright position.

Figure 6:
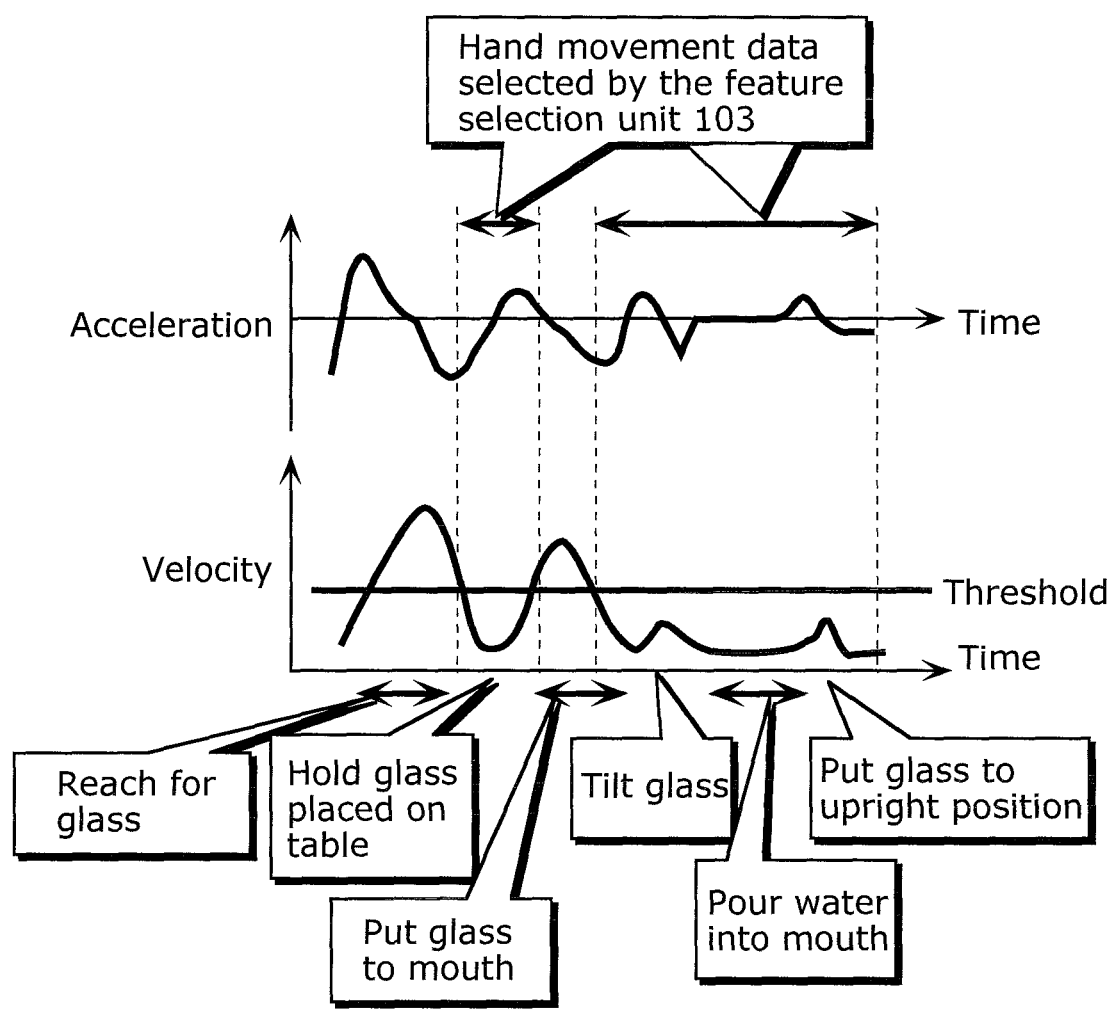
[FIG. 6]

From the hand movement data outputted from the hand movement observation unit 101, the feature selection unit 103 selects hand movement data of the time, detected by the velocity variation to detection unit 102, at which the hand velocity variation occurs (step S103). In the above example, the feature selection unit 103 selects the hand movement data of the specific times including the time at which the hand holds the glass and times before and after the hand holds the glass. A conceptual drawing at this time is shown in FIG. 6. For example, the feature selection unit 103 selects, as the hand movement data, the hand acceleration data of the specific times including the time at which the hand holds the glass and the times before and after the hand holds the glass. In step S103, a plurality of hand movement data pieces are selected. To be more specific, in the example shown in FIG. 6, in addition to the hand movement data of the time at which the hand holds the glass placed on the table, the feature selection unit 103 further selects the hand movement data of the time at which the user puts the glass to the mouth and the hand movement data of the times at which the user tilts the glass and pours the beverage into the mouth, for example. That is, the feature selection unit 103 selects the velocity data which is equal to or smaller than the threshold, among the velocity data shown in FIG. 6.

Figure 7A:
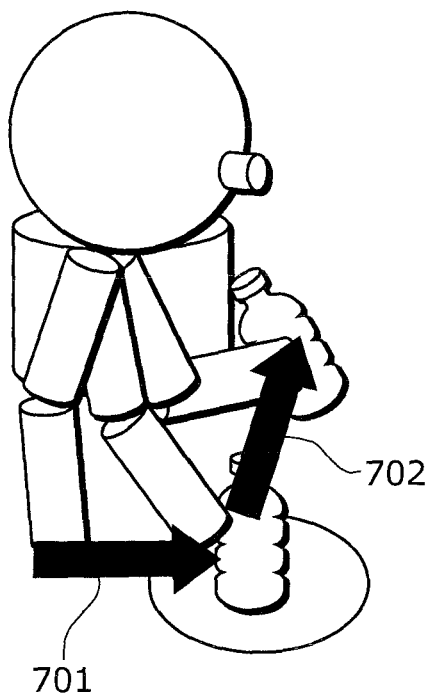
[FIG. 7A]
Figure 7B:
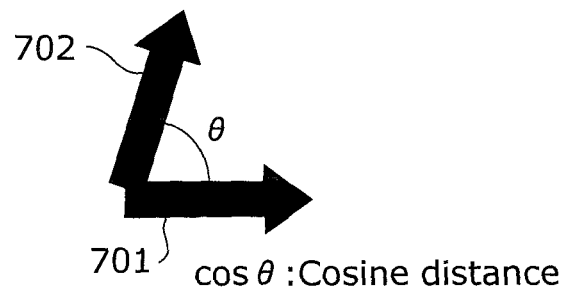
[FIG. 7B]

Moreover, there may be a case where the velocity data having a steep velocity variation is selected. As shown in FIG. 7A, whether a current velocity variation is steep can be determined by comparing a cosine distance between a velocity vector 701 at a time t−1 and a velocity vector 702 at a time t with a predetermined threshold. More specifically, when the cosine distance is smaller than the predetermined threshold, the velocity variation can be determined to be steep. On the other hand, when the cosine distance is equal to or larger than the predetermined threshold, the velocity variation can be determined not to be steep. Here, the cosine distance refers to a value of "cos θ" in the case where an angle formed by the two velocity vectors 701 and 702 is "θ", as shown in FIG. 7B. When the two velocity vectors 701 and 702 have the same direction, θ=0° and the value of the cosine distance becomes 1 which is the maximum value. When the two velocity vectors 701 and 702 have directions opposite to each other, θ=180°, and the value of the cosine distance becomes −1 which is the minimum value. In the case of the velocity data shown in FIG. 6, the time of "Hold glass placed on table" and the time of "Tilt glass" are detected by the velocity variation detection unit 102. Moreover, the velocity data around an extreme value corresponding to the time of "Hold glass placed on table" and the velocity data around an extreme value corresponding to the time of "Tilt glass" are selected by the feature selection unit 103. It should be noted that, as the aforementioned predetermined threshold, a value statistically calculated using hand movements (such as a cosine value when θ=45°) can be used. For example, each angle formed by two velocity vectors around an extreme value of velocity at the time of "Hold glass placed on table" may be sampled and thus the aforementioned predetermined threshold can be calculated according to a known statistical processing.

It should be noted that whether the current velocity variation is steep may be determined by comparing a velocity gradient difference between the velocity vectors 701 and 702 with a predetermined threshold. More specifically, when the velocity gradient difference equal to or larger than the predetermined threshold, the velocity variation can be determined to be steep. On the other hand, when the velocity gradient difference is smaller than the predetermined threshold, the velocity variation can be determined not to be steep. Here, the velocity gradient difference between the velocity vectors 701 and 702 refers to an angle formed by the velocity vectors 701 and 702. When the two velocity vectors 701 and 702 have the same direction, the velocity gradient difference "θ" is 0°. When the two velocity vectors 701 and 702 have directions opposite to each other, the velocity gradient difference θ is 180°. That is, the time at which the velocity gradient difference is equal to or larger than the predetermined threshold is detected by the velocity variation detection unit 102. It should be noted that the aforementioned predetermined threshold θ is calculated according to the same method employed for calculating the predetermined threshold of the cosine distance, and may be determined as 45°.

The behavior recognition unit 105 calculates a degree of similarity between the movement pattern data sequence and the plurality of movement data pieces selected by the feature selection unit 103, for each of the movement pattern data sequence IDs stored in the standard behavior pattern storage unit 104 (step S104). It should be noted that the degree of similarity is calculated according to a known technique and that the detailed explanation of the calculation is thus omitted.

The behavior recognition unit 105 compares the calculated degree of similarity and a specific threshold (step S105). When the degree of similarity is equal to or larger than the specific threshold (Yes in step S105), the behavior recognition unit 105 outputs the behavior label corresponding to the movement pattern data sequence having the maximum degree of similarity (step S106).

In the above example, for each of the movement pattern data sequences stored in the standard behavior pattern storage unit 104, the behavior recognition unit 105 calculates the degree of similarity between the movement pattern data sequence and the hand movement data of the specific times, selected by the feature selection unit 103, including the time at which the hand holds the glass and the times before and after the hand holds the glass. Here, the movement pattern data sequences stored in the standard behavior pattern storage unit 104 refer to: the movement pattern data sequence corresponding to the behavior "Drink beverage"; the movement pattern data sequence corresponding to the behavior "Eat food"; and the movement pattern data sequence corresponding to the behavior "Brush teeth". When the degree of similarity is smaller than the specific threshold (No in step S105), the behavior recognition unit 105 calculates the degree of similarity with the movement pattern data sequence, additionally using the hand movement data of specific times including a time at which a next velocity variation occurs and times before and after the next velocity variation occurs. Here, the time at which the next velocity variation occurs is the time of "Put glass to mouth". In this way, by calculating the degree of similarity with the movement pattern data sequence using the hand movement data pieces added one after another corresponding to the times at which the velocity variations occur, the degree of similarity is gradually increased. To be more specific, the degree of similarity is next calculated additionally using the hand movement data of the time of "Tilt glass and pour beverage into mouth", and then calculated further using the hand movement data of the time of "Put glass down". When the degree of similarity becomes equal to or larger the specific threshold (Yes in step S105), the behavior recognition unit 105 outputs the behavior label "Drink beverage" corresponding to the movement pattern data sequence having the maximum degree of similarity.

According to the behavior recognition apparatus in the first embodiment described thus far, only the hand movement data of the time at which the hand velocity variation occurs is selected as the hand movement data used for behavior recognition. On this account, behavior recognition can be performed using only the hand movement data having less environmental influences. Thus, the environmental changes, such as trajectories of the hand, do not need to be considered, meaning that the number of standard behavior pattern data pieces to be collected for behavior recognition is reduced. Moreover, since the environmental changes do not need to be considered, the user behavior can be recognized with accuracy.

(Second Embodiment)

The behavior recognition apparatus in the first embodiment detects the time at which the hand velocity variation occurs from the hand movement data, and also calculates the degree of similarity between the hand movement data and the movement pattern sequence. In the second embodiment, on the other hand, data indicating a posture of the user's arm is used in addition to the hand movement data, for detecting the time at which the hand velocity variation occurs and for calculating the degree of similarity.

Figure 8:
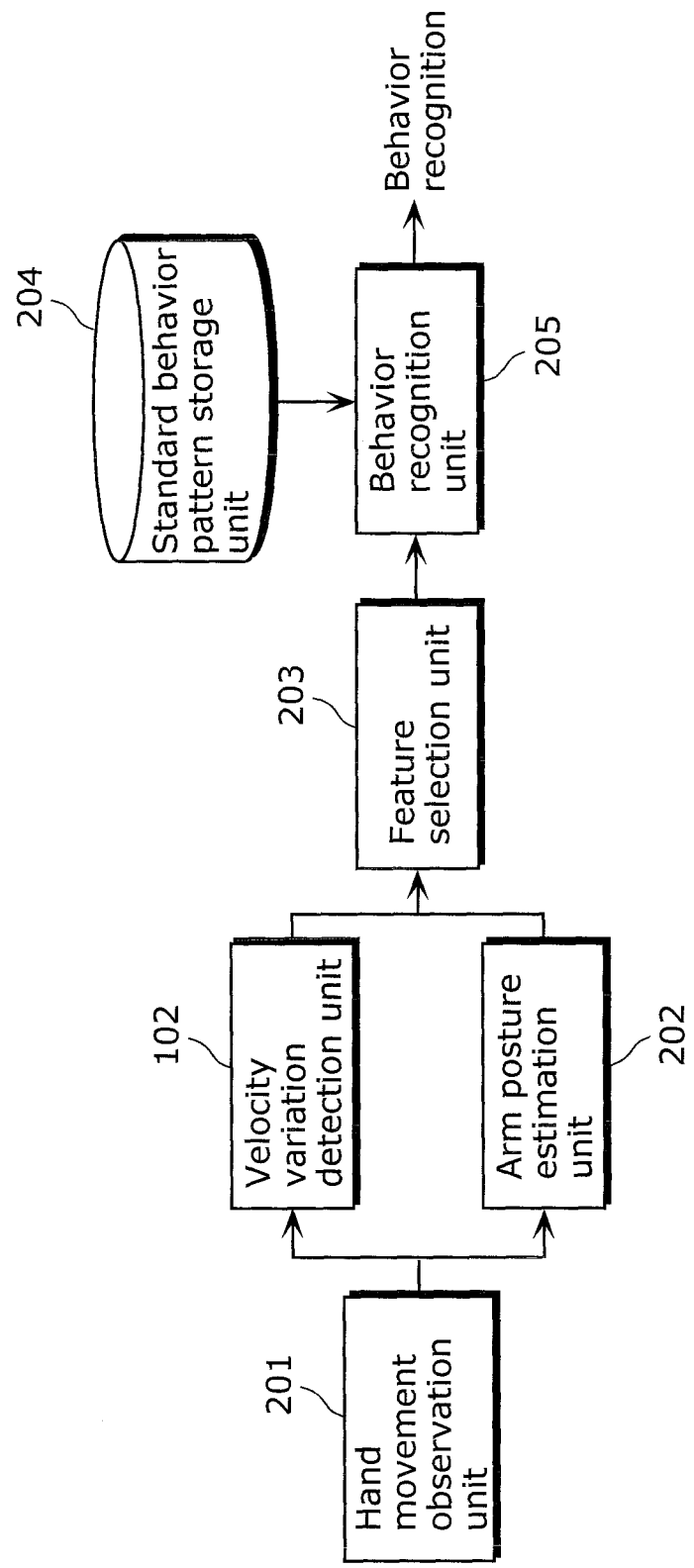
[FIG. 8]

FIG. 8 is a block diagram showing a configuration of a behavior recognition apparatus in the second embodiment. Components in the present embodiment which are identical to those in the behavior recognition apparatus in the first embodiment shown in FIG. 1 are assigned the same reference numerals used in the first embodiment. These components have the same functions and names as those in the first embodiment and, therefore, the detailed explanations are not repeated here.

The behavior recognition apparatus in the second embodiment includes a hand movement observation unit 201, a velocity variation detection unit 102, an arm posture estimation unit 202, a feature selection unit 203, a standard behavior pattern storage unit 204, and a behavior recognition unit 205.

As is the case with the hand movement observation unit 101, the hand movement observation unit 201 outputs, as the hand movement data, the acceleration data, angular velocity data, and velocity data of the hand. In addition, the hand movement observation unit 201 senses accelerations and angular velocities outputted from acceleration sensors and angular velocity sensors attached to each of the forearm, upper arm, and shoulder of the user. Then, the hand movement observation unit 201 outputs the sensing result as the hand movement data.

The arm posture estimation unit 202 estimates each angle of an elbow joint and a shoulder joint from the accelerations and angular velocities of the forearm, upper arm, and shoulder included in the hand movement data outputted from the hand movement observation unit 201, and thus estimates the arm posture relative to the user's body. Here, each angle of a wrist joint, elbow joint, and shoulder joint may be sensed using an optical motion capture device. It should be noted that any implementation unit can be used in the present invention as long as the angles of the wrist joint, elbow joint, and shoulder joint are obtained.

The feature selection unit 203 selects the hand movement data to be used for behavior recognition, using the data indicating the velocity variation detected by the velocity variation detection unit 102 and the data indicating the arm posture estimated by the arm posture estimation unit 202. To be more specific, when the arm posture estimated by the arm posture estimation unit 202 matches a predetermined arm posture and the velocity variation detection unit 102 detects a time at which a velocity variation occurs, the feature selection unit 203 selects the hand movement data of the time, detected by the velocity variation detection unit 102, at which the velocity variation occurs.

The standard behavior pattern storage unit 204 stores, for each of behaviors of the user, a pair of: a movement pattern data sequence in which the present movement is represented by a hand movement data sequence of times at which the variations in the hand velocity occur; and an arm posture of the times at which the variations in the hand velocity occur. As shown in FIG. 9, the standard behavior pattern storage unit 204 stores, for each of the behaviors of the user, a movement pattern data sequence ID, a behavior label, a movement pattern data sequence, and an arm posture. The movement pattern data sequence ID, the behavior label, and the movement pattern data sequence are the same as those stored in the standard behavior pattern storage unit 104 shown in FIG. 2 in the first embodiment. The arm posture refers to a posture of the arm when the user performs a behavior. As an example, the arm posture corresponding to the behavior "Drink beverage" is indicated as "Hand: in front of chest or mouth".

The behavior recognition unit 205 calculates a degree of similarity between: the pair of the movement pattern data sequence and the arm posture stored in the standard behavior pattern storage unit 204; and the hand movement data selected by the feature selection unit 203 and the arm posture, estimated by the arm posture estimation unit 202, corresponding to the time at which the hand velocity variation occurs. Moreover, the behavior recognition unit 105 outputs the behavior label corresponding to the pair having the highest degree of similarity, and accordingly recognizes the behavior of the user.

Figure 10:
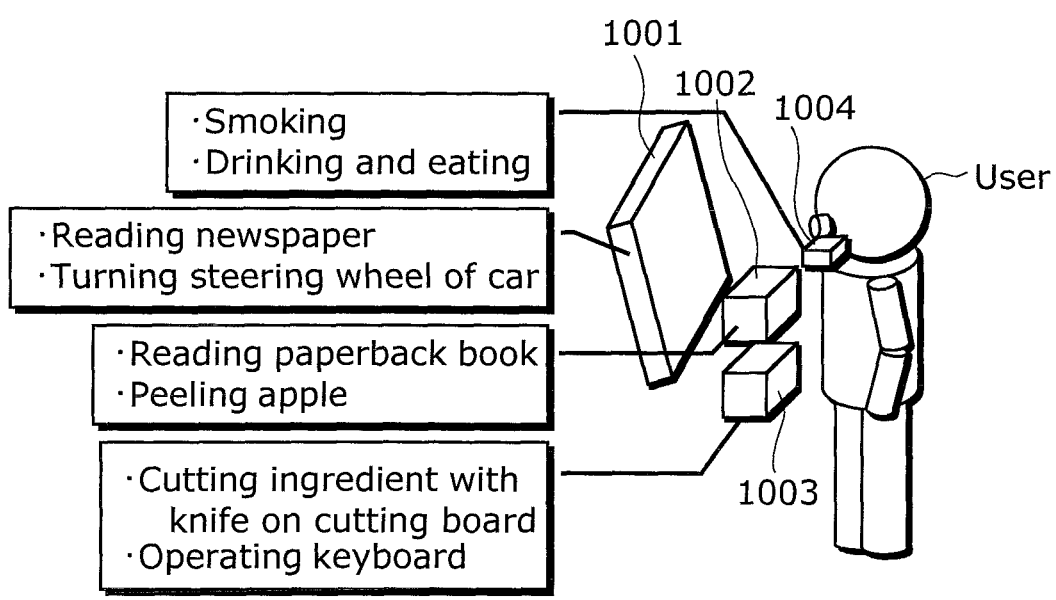
[FIG. 10]

The inventive concept of the present embodiment is explained, with reference to FIG. 10. A location where the user efficiently uses a tool or an object (such as a location where the user can easily apply a force or a location where the user can easily see the object) has been predetermined. To be more specific, a behavior achieved using a tool or an object can be associated with a space relative to the user's body. On account of this, the behavior performed by the user can be identified to some extent on the basis of the arm posture of the user, which is thus to be used for behavior recognition. As one example, the space relative to the user's body can be obtained as follows. In the case where the user uses a specific tool multiple times, locations where the user uses this tool are sensed and averaged. Then, a set of locations, each being equal to or larger than a specific threshold, can be determined as the space relative to the user's body. For obtaining the space relative to the user's body, the sensing target does not need to be always the same user and may be a different person.

Figure 11:
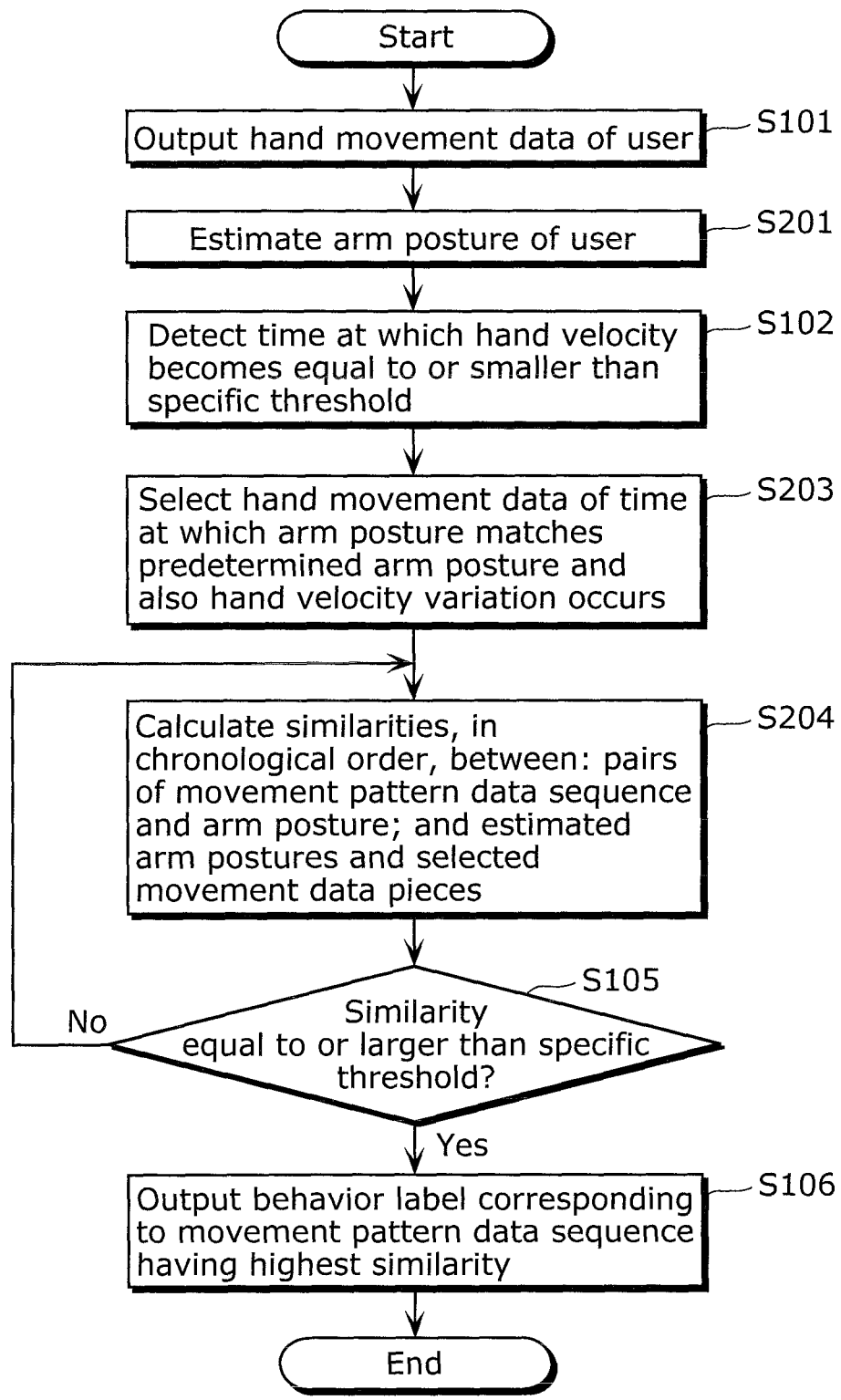
[FIG. 11]

An example of an operation performed by the behavior recognition apparatus configured as described above in the present embodiment is explained as follows. FIG. 11 is a flowchart showing processing performed by the behavior recognition apparatus in the present embodiment. Processes which are identical to those in the processing performed by the behavior recognition apparatus as shown in FIG. 3 in the first embodiment are assigned the same step numbers used in the first embodiment.

The hand movement observation unit 201 senses a hand movement made by the user and then outputs the hand movement data (i.e., the acceleration data, angular velocity data, and velocity data of the hand, and the accelerations and angular velocities of the forearm, upper arm, and shoulder) (step S101).

The arm posture estimation unit 202 estimates the angles of the elbow and shoulder joints, on the basis of the accelerations and angular velocities of the forearm, upper arm, and shoulder among the hand movement data outputted from the hand movement observation unit 201 (step S201). For example, when the user is reading a newspaper, a position of the user's hand estimated by the arm posture estimation unit 202 is located in an area 1001 which is in front of the user's body.

From the hand movement data outputted from the hand movement observation unit 201, the velocity variation detection unit 102 detects a time at which a hand velocity variation occurs, such as a time at which the hand velocity becomes equal to or smaller than a specific threshold (step S102).

When the arm posture estimated by the arm posture estimation unit 202 matches a predetermined arm posture and the velocity variation detection unit 102 detects a time at which a velocity variation occurs, the feature selection unit 203 selects the hand movement data of the time, detected by the velocity variation detection unit 102, at which the velocity variation occurs (step S203). Here, the predetermined arm posture includes all arm postures which the behavior recognition apparatus assumes can be taken by a human body. For example, the predetermined arm posture refers to an arm posture in which the user's hand is located in one of areas 1001 to 1004 shown in FIG. 10. Examples of the hand movement data are as described in the first embodiment.

Examples of the hand movement data to be selected by the feature selection unit 203 for behavior recognition from the hand movement data outputted from the hand movement observation unit 201 include the following. Suppose that the arm posture estimation unit 202 estimates that the position of the user's hand is located within a 1-meter square in front of the user's body (i.e., within one of the areas 1001 to 1004) and a detection time of the hand movement data matches the time, detected by the velocity variation detection unit 102, at which the hand velocity variation occurs. In this case, the feature selection unit 203 selects the hand movement data to be used for behavior recognition from the hand movement data outputted from the hand movement observation unit 201. Thus, only the hand movement data of the time at which the hand touches the body or at which the hand velocity variation occurs when the hand is located in a position that is considered important as a hand position (for example, the hand is located in front of the chest when peeling a fruit using a knife, and in front of the hip when cutting an ingredient using a knife). That is to say, in the case where the hand movement is observed at all times, a velocity variation point considered important because of the present hand position can be selected from among velocity variation points (the times at which the hand velocity variations occur) which occur with a high frequency.

In the above example, the area considered important as the hand position is a 1-meter square in front of the user's body. However, the area considered important may be subdivided, corresponding to the cases, for example, where the hand is in front of the chest, the hand is in front of the hip, and the hand is touching the body. With this subdivision, it becomes possible to select only the hand movement data of the time at which the hand velocity variation is detected and the hand is in front of the chest.

The behavior recognition unit 205 calculates, for each of the movement pattern data sequence IDs stored in the standard behavior pattern storage unit 204, a degree of similarity between: the pair of the movement pattern data sequence and the arm posture; and the hand movement data selected by the feature selection unit 203 and the arm posture, estimated by the arm posture estimation unit 202, corresponding to the time at which the hand velocity variation occurs (step S204). For example, only when the arm posture stored in the standard behavior pattern storage unit 204 matches the arm posture estimated by the arm posture estimation unit 202, the degree of similarity between the movement pattern data sequence and the hand movement data is calculated. Otherwise, the degree of similarity is calculated at 0. It should be noted that the degree of similarity is calculated according to a known technique and that the detailed explanation of the calculation is thus omitted.

The behavior recognition unit 205 compares the calculated degree of similarity and a specific threshold (step S105). When the degree of similarity is equal to or larger than the specific threshold (Yes in step S105), the behavior recognition unit 205 outputs the behavior label corresponding to the movement pattern data sequence having the maximum degree of similarity (step S106).

According to the behavior recognition apparatus in the second embodiment described thus far, only the hand movement data of the time at which the arm posture matches the predetermined arm posture and also the hand velocity variation occurs is selected as the hand movement data used for behavior recognition. Here, the arm posture is used for behavior recognition as well. Therefore, the behavior recognition can be achieved with consideration given to the hand position taken when the behavior is performed. On this account, as compared to the first embodiment, the user behavior can be recognized more accurately.

(Third Embodiment)

The behavior recognition apparatus in the second embodiment selects the hand movement data and calculates the degree of similarity, on the basis of the hand movement data and the arm posture. In the third embodiment, on the other hand, the selection of the hand movement data and the calculation of the degree of similarity are performed further on the basis of a body posture.

Figure 12:
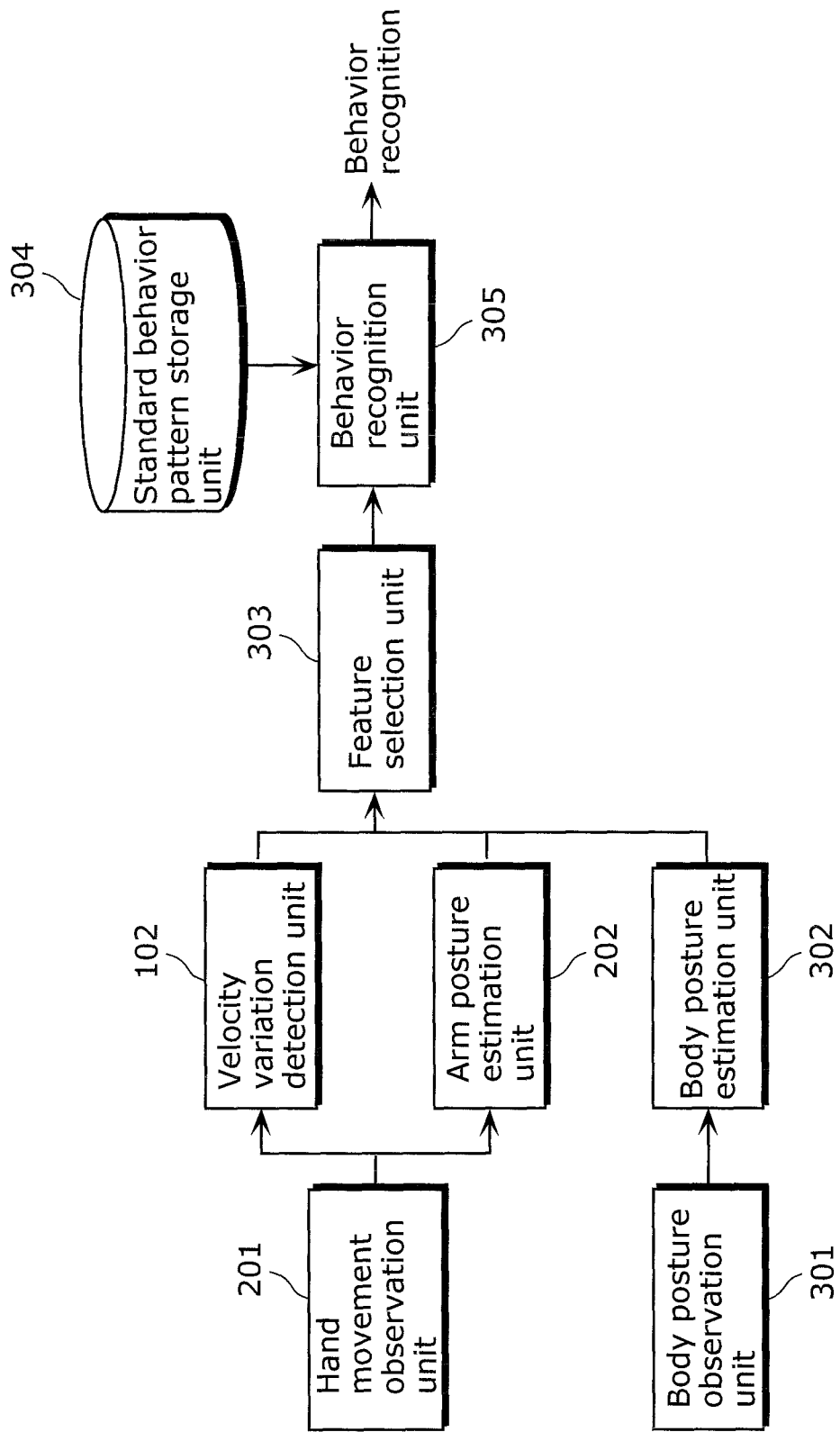
[FIG. 12]

FIG. 12 is a block diagram showing a configuration of a behavior recognition apparatus in the third embodiment. Components in the present embodiment which are identical to those in the behavior recognition apparatuses in the first and second embodiments are assigned the same reference numerals used in the first and second embodiments.

The behavior recognition apparatus in the third embodiment includes a hand movement observation unit 201, a velocity variation detection unit 102, an arm posture estimation unit 202, a body posture observation unit 301, a body posture estimation unit 302, a feature selection unit 303, a standard behavior pattern storage unit 304, and a behavior recognition unit 305.

The body posture observation unit 301 is configured with an input device, including an acceleration sensor and an angular velocity sensor, which senses a hip movement. When the user moves the hip, the body posture observation unit 301 outputs the hip movement data that includes acceleration data, angular velocity data, and velocity data in three axes (that is, X, Y, and Z directions). The body posture observation unit 301 is worn on the hip of the user, for example.

The body posture estimation unit 302 can determine a body posture of the user on the basis of the hip movement data outputted from the body posture observation unit 301. The body posture is different between when the user puts the hand near the head and moves the hand backward from the front in a standing position and when the user puts the hand near the head and moves the hand backward from the front in a lying position. Thus, it can be determined that the user is standing in the former case and is lying in the latter case.

The feature selection unit 303 may select the hand movement data to be used for behavior recognition from the hand movement data outputted from the hand movement observation unit 201, using the data indicating the velocity variation detected by the velocity variation detection unit 102, the data indicating the arm posture estimated by the arm posture estimation unit 202, and the data indicating the body posture estimated by the body posture estimation unit 302. To be more specific, when: the arm posture estimated by the arm posture estimation unit 202 matches a predetermined arm posture; the body posture estimated by the body posture estimation unit 302 matches a predetermined body posture; and the velocity variation detection unit 102 detects a time at which a velocity variation occurs, the feature selection unit 303 selects the hand movement data of the time, detected by the velocity variation detection unit 102, at which the velocity variation occurs. For example, when the arm posture indicates that the user's hand is located in front of the chest and the body posture of the user is the standing position, the feature selection unit 303 selects the hand movement data of the time at which the velocity variation occurs. Thus, for example, in the case where the hand movement which is possible only in the standing position occurs in the lying position, the body posture can be set as a condition used when the feature selection unit 303 selects the movement data. This allows only the hand movement data more related to the behavior to be selected.

The standard behavior pattern storage unit 304 stores, for each of behaviors of the user, a combination of: a movement pattern data sequence in which the present movement is represented by a hand movement data sequence of times at which the variations in the hand velocity occur; an arm posture of the times at which the variations in the hand velocity occur; and a body posture of the times at which the variations in the hand velocity occur. As shown in FIG. 13, the standard behavior pattern storage unit 304 stores, for each of the behaviors of the user, a movement pattern data sequence ID, a behavior label, a movement pattern data sequence, an arm posture, and a body posture. The movement pattern data sequence ID, the behavior label, the movement pattern data sequence, and the arm posture are the same as those stored in the standard behavior pattern storage unit 204 shown in FIG. 9 in the second embodiment. The body posture refers to a posture of the body when the user performs a behavior. As an example, the body posture corresponding to the behavior "Drink beverage" is indicated as "Standing position".

The behavior recognition unit 305 calculates a degree of similarity between: the combination of the movement pattern data sequence, arm posture, and body posture stored in the standard behavior pattern storage unit 304; and the hand movement data selected by the feature selection unit 303, the arm posture, estimated by the arm posture estimation unit 202, corresponding to the time at which the hand velocity variation occurs, and the body posture, estimated by the body posture estimation unit 302, corresponding to the time at which the hand velocity variation occurs. Then, the behavior recognition unit 305 outputs the behavior label corresponding to the combination having the highest degree of similarity, and accordingly recognizes the behavior of the user.

Figure 14:
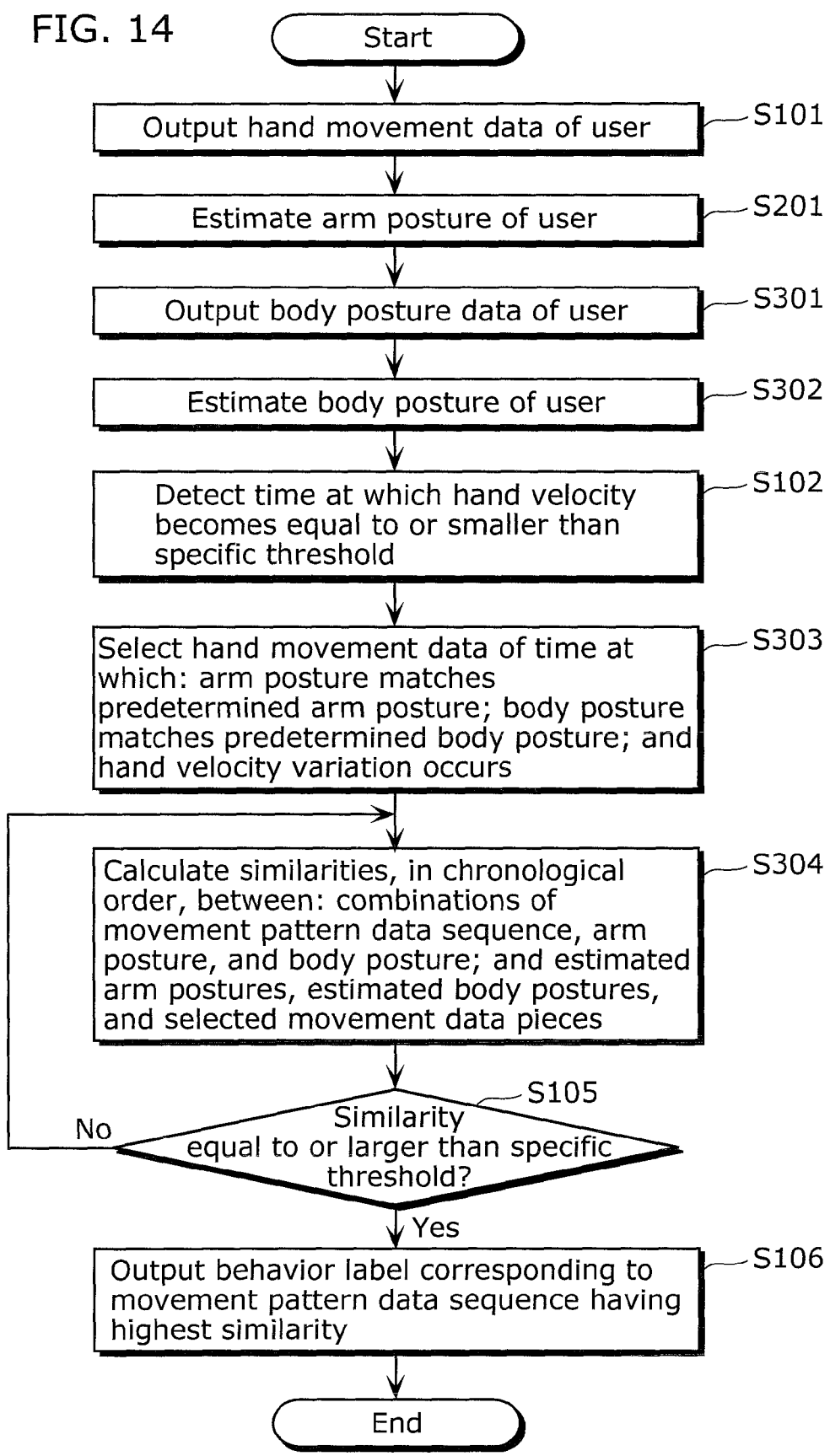
[FIG. 14]

An example of an operation performed by the behavior recognition apparatus configured as described above in the present embodiment is explained as follows. FIG. 14 is a flowchart showing processing performed by the behavior recognition apparatus in the present embodiment. Processes which are identical to those in the processing performed by each of the behavior recognition apparatuses in the first and second embodiments are assigned the same step numbers used in the first and second embodiments.

The hand movement observation unit 201 senses a hand movement made by the user and then outputs the hand movement data (i.e., the acceleration data, angular velocity data, and velocity data of the hand, and the accelerations and angular velocities of the forearm, upper arm, and shoulder) (step S101).

The arm posture estimation unit 202 estimates the angles of the elbow and shoulder joints, on the basis of the accelerations and angular velocities of the forearm, upper arm, and shoulder among the hand movement data outputted from the hand movement observation unit 201, and then estimates the arm posture relative to the user's body (step S201).

The body posture observation unit 301 senses a hip movement and outputs hip movement data (step S301).

The body posture estimation unit 302 estimates a body posture of the user on the basis of the hip movement data outputted from the body posture observation unit 301 (S302).

From the hand movement data outputted from the hand movement observation unit 201, the velocity variation detection unit 102 detects a time at which a hand velocity variation occurs, such as a time at which the hand velocity becomes equal to or smaller than a specific threshold (step S102).

When: the arm posture estimated by the arm posture estimation unit 202 matches a predetermined arm posture; the body posture estimated by the body posture estimation unit 302 matches a predetermined body posture; and the velocity variation detection unit 102 detects a time at which a velocity variation occurs, the feature selection unit 303 selects the hand movement data of the time, detected by the velocity variation detection unit 102, at which the velocity variation occurs (step S303). Here, the predetermined body posture refers to the standing position, for example.

The behavior recognition unit 305 calculates, for each of the movement pattern data sequence IDs stored in the standard behavior pattern storage unit 304, a degree of similarity between: the combination of the movement pattern data sequence, arm posture, and body posture; and the hand movement data selected by the feature selection unit 303, the arm posture, estimated by the arm posture estimation unit 202, corresponding to the time at which the hand velocity variation occurs, and the body posture, estimated by the body posture estimation unit 302, corresponding to the time at which the hand velocity variation occurs (step S304). For example, only when the arm posture stored in the standard behavior pattern storage unit 304 matches the arm posture estimated by the arm posture estimation unit 202 and also the body posture stored in the standard behavior pattern storage unit 304 matches the body posture estimated by the body posture estimation unit 302, the degree of similarity between the movement pattern data sequence and the hand movement data is calculated. Otherwise, the degree of similarity is calculated at 0. It should be noted that the degree of similarity is calculated according to a known technique and that the detailed explanation of the calculation is thus omitted.

The behavior recognition unit 305 compares the calculated degree of similarity and a specific threshold (step S105). When the degree of similarity is equal to or larger than the specific threshold (Yes in step S105), the behavior recognition unit 305 outputs the behavior label corresponding to the movement pattern data sequence having the maximum degree of similarity (step S106).

According to the behavior recognition apparatus in the third embodiment described thus far, when: the arm posture matches the predetermined arm posture; the body posture matches the predetermined body posture; and the hand velocity variation occurs, only the hand movement data of the detected time at which the hand velocity variation occurs is selected as the hand movement data used for behavior recognition. Here, the data indicating the arm posture and the data indicating the body posture are used for behavior recognition as well. Therefore, the behavior recognition can be achieved with consideration given to the hand position taken when the behavior is performed. On this account, as compared to the first embodiment, the user behavior can be recognized more accurately.

(Fourth Embodiment)

The behavior recognition apparatus in the second embodiment selects the hand movement data and calculates the degree of is similarity, on the basis of the hand movement data and the arm posture. In the fourth embodiment, on the other hand, instead of the arm posture, a state of gripping an object is used. Thus, the selection of the hand movement data and the calculation of the degree of similarity are performed on the basis of the hand movement data and the object grip state.

Figure 15:
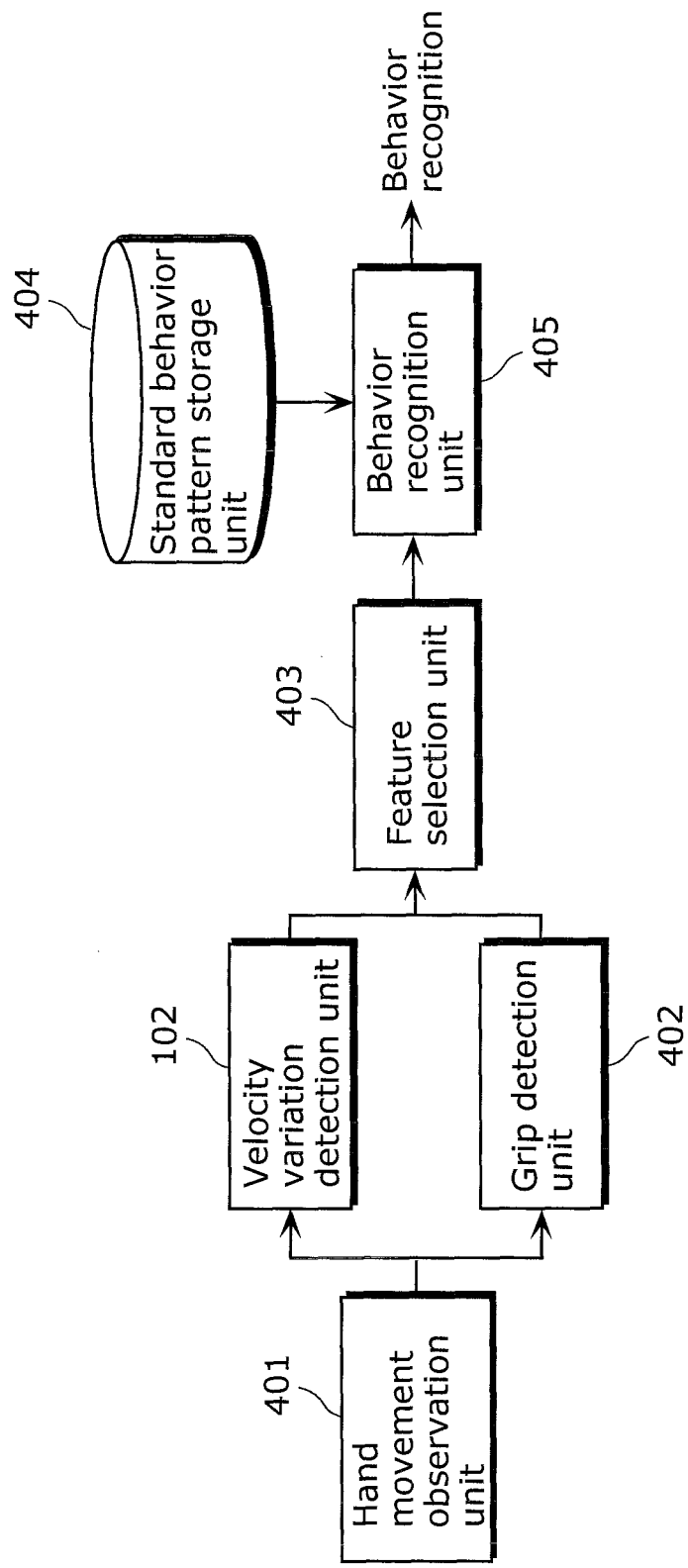
[FIG. 15]

FIG. 15 is a block diagram showing a configuration of a behavior recognition apparatus in the fourth embodiment. Components in the present embodiment which are identical to those in the behavior recognition apparatuses in the above embodiments are assigned the same reference numerals used in the above embodiments. These components have the same functions and names as those in the above embodiments and, therefore, the detailed explanations are not repeated here.

The behavior recognition apparatus in the fourth embodiment includes a hand movement observation unit 401, a velocity variation detection unit 102, a grip detection unit 402, a feature selection unit 403, a standard behavior pattern storage unit 404, and a behavior recognition unit 405.

As is the case with the hand movement observation unit 101, the hand movement observation unit 401 outputs, as the hand movement data, the acceleration data, angular velocity data, and velocity data of the hand. In addition, the hand movement observation unit 401 senses an electric potential of a hand muscle and then outputs hand myoelectric information.

The grip detection unit 402 estimates a grip state which refers to a state of gripping an object by the hand, on the basis of the hand myoelectric information outputted from the hand movement observation unit 401.

The feature selection unit 403 selects the hand movement data to be used for behavior recognition, using the data indicating the velocity variation detected by the velocity variation detection unit 102 and the data indicating the grip state estimated by the grip detection unit 402. To be more specific, when the grip state estimated by the grip detection unit 402 matches a predetermined grip state and the velocity variation detection unit 102 detects a time at which a velocity variation occurs, the feature selection unit 403 selects the hand movement data of the time, detected by the velocity variation detection unit 102, at which the velocity variation occurs.

The standard behavior pattern storage unit 404 stores, for each of behaviors of the user, a pair of: a movement pattern data sequence in which the present movement is represented by a hand movement data sequence of times at which the variations in the hand velocity occur; and a grip state of the times at which the variations in the hand velocity occur. As shown in FIG. 16, the standard behavior pattern storage unit 404 stores, for each of the behaviors of the user, a movement pattern data sequence ID, a behavior label, a movement pattern data sequence, and a grip state. The movement pattern data sequence ID, the behavior label, and the movement pattern data sequence are the same as those stored in the standard behavior pattern storage unit 204 shown in FIG. 2 in the first embodiment. The grip state refers to a state of gripping an object when the user performs a behavior. As an example, the grip state corresponding to the behavior "Drink beverage" is indicated as "Grip".

The behavior recognition unit 405 calculates a degree of similarity between: the pair of the movement pattern data sequence and grip state stored in the standard behavior pattern storage unit 404; and the hand movement data selected by the feature selection unit 403 and the grip state, estimated by the grip detection unit 402, corresponding to the time of the time at which the hand velocity variation occurs. Then, the behavior recognition unit 405 outputs the behavior label corresponding to the pair having the highest degree of similarity, and accordingly recognizes the behavior of the user.

Figure 17:
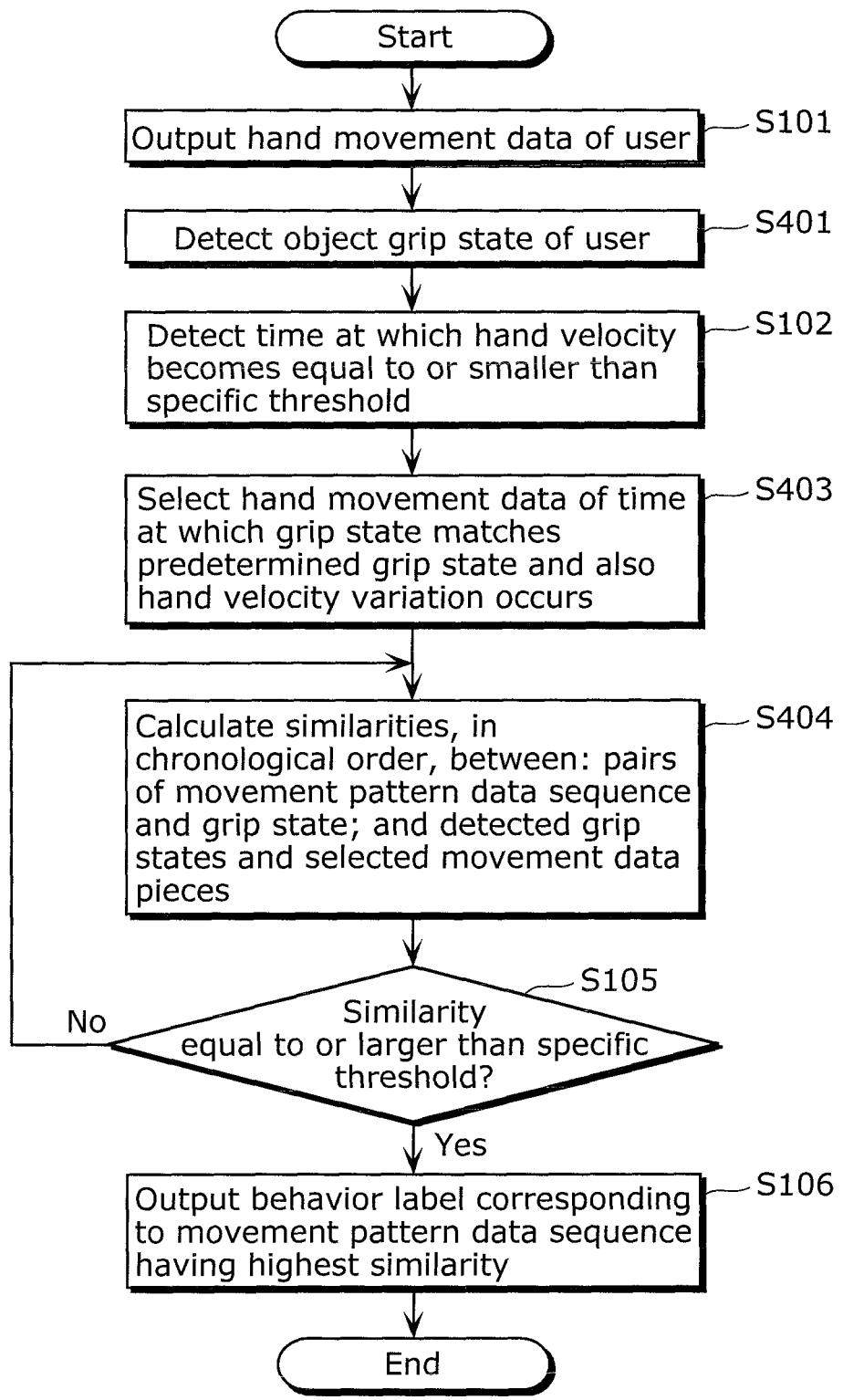
[FIG. 17]

An example of an operation performed by the behavior recognition apparatus configured as described above in the present embodiment is explained as follows. FIG. 17 is a flowchart showing processing performed by the behavior recognition apparatus in the present embodiment. Processes which are identical to those in the processing performed by each of the behavior recognition apparatuses in the above embodiments are assigned the same step numbers used in the above embodiments.

The hand movement observation unit 401 outputs, as the hand movement data, the acceleration data, angular velocity data, and velocity data of the hand. In addition, the hand movement observation unit 401 senses the electric potential of the hand muscle and then outputs the hand myoelectric information (step S101).

The grip detection unit 402 estimates whether or not the hand is in the grip state where the hand is gripping the object, on the basis of the hand myoelectric information outputted from the hand movement observation unit 401 (step S401).

From the hand movement data outputted from the hand movement observation unit 401, the velocity variation detection unit 102 detects a time at which a hand velocity variation occurs, such as a time at which the hand velocity becomes equal to or smaller than a specific threshold (step S102).

When the grip state estimated by the grip detection unit 402 matches a predetermined grip state and the velocity variation detection unit 102 detects a time at which a velocity variation occurs, the feature selection unit 403 selects the hand movement data of the time, detected by the velocity variation detection unit 102, at which the velocity variation occurs (step S403). Here, the predetermined grip state includes "Grip" indicating that the hand is gripping an object, for example. Thus, only the movement data of the time at which the hand velocity variation occurs while the user is gripping an object to use the object, can be selected. That is to say, in the case where the hand movement is observed at all times, a velocity variation point considered important because of the present grip state can be selected from among velocity variation points which occur with a high frequency.

The behavior recognition unit 405 calculates, for each of the movement pattern data sequence IDs stored in the standard behavior pattern storage unit 404, a degree of similarity between: the pair of the movement pattern data sequence and grip state; and the hand movement data selected by the feature selection unit 403 and the grip state, estimated by the grip detection unit 402, corresponding to the time at which the hand velocity variation occurs (step S404). For example, only when the grip state stored in the standard behavior pattern storage unit 404 matches the grip state estimated by the grip detection unit 402, the degree of similarity between the movement pattern data sequence and the hand movement data is calculated. Otherwise, the degree of similarity is calculated at 0. It should be noted that the degree of similarity is calculated according to a known technique and that the detailed explanation of the calculation is thus omitted.

The behavior recognition unit 405 compares the calculated degree of similarity and a specific threshold (step S105). When the degree of similarity is equal to or larger than the specific threshold (Yes in step S105), the behavior recognition unit 405 outputs the behavior label corresponding to the movement pattern data sequence having the maximum degree of similarity (step S106).

According to the behavior recognition apparatus in the fourth embodiment described thus far, only the hand movement data of the time at which the grip state matches the predetermined grip state and also the hand velocity variation occurs is selected as the hand movement data used for behavior recognition. Here, the object grip state is used for behavior recognition as well. Therefore, the behavior recognition can be achieved with consideration given to the object grip state in which the behavior is performed. On this account, as compared to the first embodiment, the user behavior can be recognized more accurately.

(Fifth Embodiment)

In the fifth embodiment, the selection of hand movement data and the calculation of a degree of similarity are performed on the basis of hand movement data, an arm posture of the user, and an object grip state.

Figure 18:
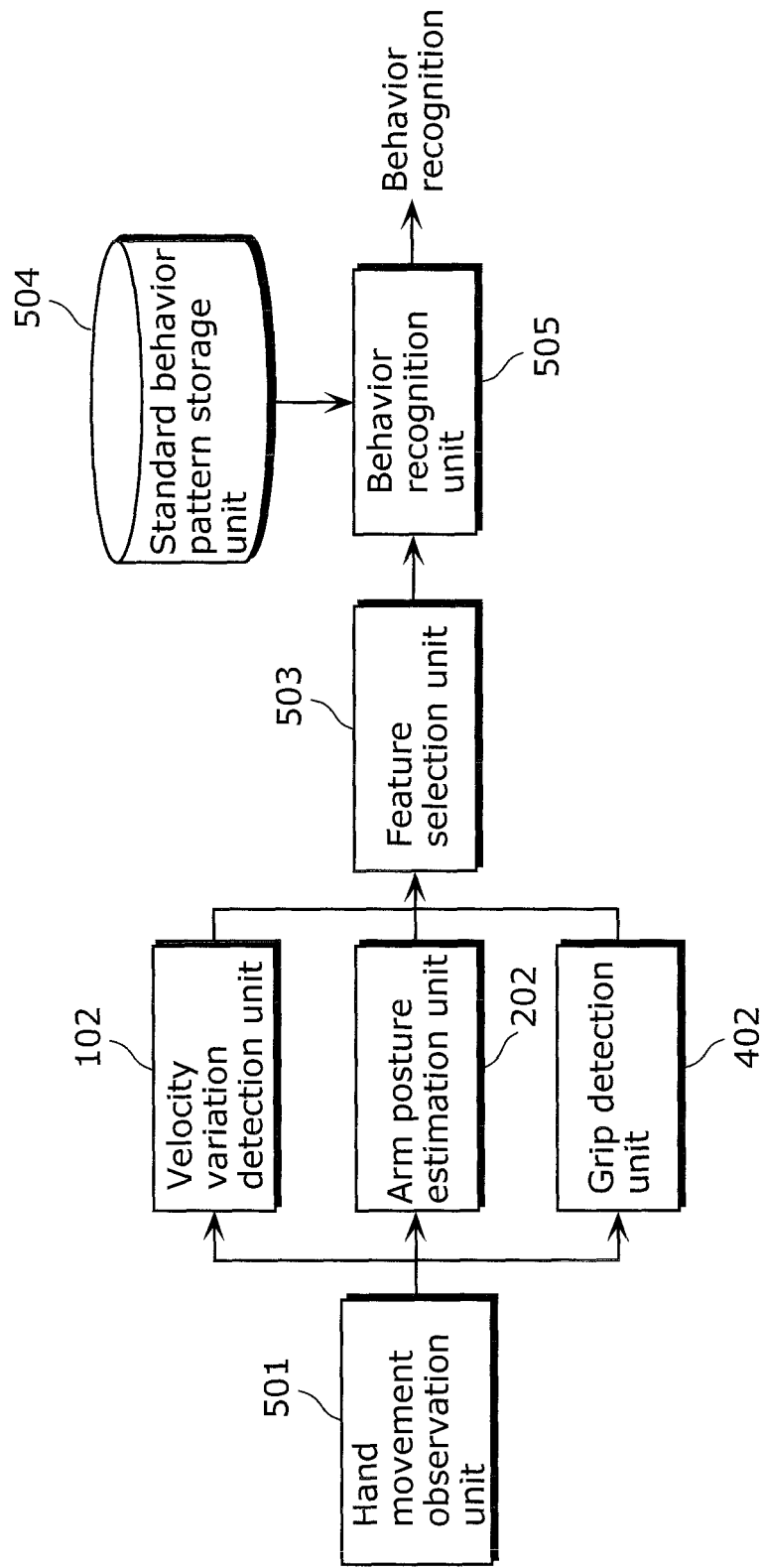
[FIG. 18]

FIG. 18 is a block diagram showing a configuration of a behavior recognition apparatus in the fifth embodiment. Components in the present embodiment which are identical to those in the behavior recognition apparatuses in the above embodiments are assigned the same reference numerals used in the above embodiments. These components have the same functions and names as those in the above embodiments and, therefore, the detailed explanations are not repeated here.

The behavior recognition apparatus in the fifth embodiment includes a hand movement observation unit 501, a velocity variation detection unit 102, an arm posture estimation unit 202, a grip detection unit 402, a feature selection unit 503, a standard behavior pattern storage unit 504, and a behavior recognition unit 505.

As is the case with the hand movement observation unit 101, the hand movement observation unit 501 outputs, as the hand movement data, the acceleration data, angular velocity data, and velocity data of the hand. In addition, the hand movement observation unit 501 senses accelerations and angular velocities of each of the forearm, upper arm, and shoulder of the user. Then, the hand movement observation unit 501 outputs the sensing result as the hand movement data. Moreover, the hand movement observation unit 501 senses an electric potential of a hand muscle and then outputs hand myoelectric information. In other words, the hand movement observation unit 501 has the functions of both the hand movement observation unit 201 and the hand movement observation unit 401.

The feature selection unit 503 selects the hand movement data to be used for behavior recognition, using the data indicating the velocity variation detected by the velocity variation detection unit 102, the data indicating the arm posture estimated by the arm posture estimation unit 202, and the data indicating the grip state estimated by the grip detection unit 402. To be more specific, when: the arm posture estimated by the arm posture estimation unit 202 matches a predetermined arm posture; the grip state estimated by the grip detection unit 402 matches a predetermined grip state; and the velocity variation detection unit 102 detects a time at which a velocity variation occurs, the feature selection unit 503 selects the hand movement data of the time, detected by the velocity variation detection unit 102, at which the velocity variation occurs.

The standard behavior pattern storage unit 504 stores, for each of behaviors of the user, a combination of: a movement pattern data sequence in which the present movement is represented by a hand movement data sequence of times at which the variations in the hand velocity occur; an arm posture of the times at which the variations in the hand velocity occur; and a grip state of the times at which the variations in the hand velocity occur. As shown in FIG. 19, the standard behavior pattern storage unit 504 stores, for each of the behaviors of the user, a movement pattern data sequence ID, a behavior label, a movement pattern data sequence, an arm posture, and a grip state. "Arm posture" and "Grip state" have been explained in the above embodiments. As an example, "Arm posture" and "Grip state" corresponding to the behavior "Drink beverage" are indicated as "Hand: in front of chest" and "Grip", respectively.

The behavior recognition unit 505 calculates a degree of similarity between: the combination of the movement pattern data sequence, arm posture, and grip stat stored in the standard behavior pattern storage unit 504; and the hand movement data selected by the feature selection unit 503, the arm posture, estimated by the arm posture estimation unit 202, corresponding to the time at which the hand velocity variation occurs, and the grip state, estimated by the grip detection unit 402, corresponding to the time at which the hand velocity variation occurs. Then, the behavior recognition unit 505 outputs the behavior label corresponding to the combination having the highest degree of similarity, and accordingly recognizes the behavior of the user.

An example of an operation performed by the behavior recognition apparatus configured as described above in the present embodiment is explained as follows. FIG. 20 is a flowchart showing processing performed by the behavior recognition apparatus in the present embodiment. Processes which are identical to those in the processing performed by each of the behavior recognition apparatuses in the above embodiments are assigned the same step numbers used in the above embodiments.

The hand movement observation unit 501 senses a hand movement made by the user and then outputs the hand movement data (that is: the acceleration data, angular velocity data, and velocity data of the hand; the accelerations and angular velocities of the forearm, upper arm, and shoulder; and the hand myoelectric information) (step S101).

The arm posture estimation unit 202 estimates the angles of the elbow and shoulder joints, on the basis of the accelerations and angular velocities of the forearm, upper arm, and shoulder among the hand movement data outputted from the hand movement observation unit 201. Moreover, the arm posture estimation unit 202 estimates the arm posture relative to the user's body, on the basis of the angles is of the elbow and shoulder joints (step S201).

The grip detection unit 402 estimates whether or not the hand is in the grip state where the hand is gripping the object, on the basis of the hand myoelectric information outputted from the hand movement observation unit 501 (step S401).

From the hand movement data outputted from the hand movement observation unit 501, the velocity variation detection unit 102 detects a time at which a hand velocity variation occurs, such as a time at which the hand velocity becomes equal to or smaller than a specific threshold (step S102).

When: the arm posture estimated by the arm posture estimation unit 202 matches a predetermined arm posture; the grip state estimated by the grip detection unit 402 matches a predetermined grip state; and the velocity variation detection unit 102 detects a time at which a velocity variation occurs, the feature selection unit 503 selects the hand movement data of the time, detected by the velocity variation detection unit 102, at which the velocity variation occurs (step S503). As one example, suppose that the arm posture estimated by the arm posture estimation unit 202 indicates that the position of the user's hand is located within a 1-meter square in front of the user's body and also the grip state estimated by the grip detection unit 402 indicates that the user's hand is gripping an object. In this case, when the velocity variation detection unit 102 detects a time at which a hand velocity variation occurs, the feature selection unit 503 selects the hand movement data of the time, detected by the velocity variation detection unit 102, at which the hand velocity variation occurs, from the hand movement data outputted from the hand movement observation unit 501. Thus, when the user is gripping an object to use the object, only the movement data of the time at which the hand touches the body or the hand is located in a position that is considered important as a hand position and also the hand velocity variation occurs, can be selected. Examples of locations considered important as the hand position includes: in front of the chest when peeling a fruit using a knife and in front of the hip when cutting an ingredient using a knife. That is to say, in the case where the hand movement is observed at all times, a velocity variation point considered important because of the present hand position can be selected from among velocity variation points which occur with a high frequency. In the above example, the area considered important as the hand position is a 1-meter square in front of the user's body. However, the area considered important may be subdivided, corresponding to the cases, for example, where the hand is in front of the chest, the hand is in front of the hip, and the hand is touching the body.

The behavior recognition unit 505 calculates, for each of the movement pattern data sequence IDs stored in the standard behavior pattern storage unit 504, a degree of similarity between: the combination of the movement pattern data sequence, arm posture, and grip state; and the hand movement data selected by the feature selection unit 503, the arm posture, estimated by the arm posture estimation unit 202, corresponding to the time at which the hand velocity variation occurs, and the grip state, estimated by the grip detection unit 402, corresponding to the time at which the hand velocity variation occurs (step S504). For example, only when the arm posture and grip state stored in the standard behavior pattern storage unit 504 match the arm posture estimated by the arm posture estimation unit 202 and the grip state estimated by the grip detection unit 402 respectively, the behavior recognition unit 505 calculates the degree of similarity between the movement pattern data sequence and the hand movement data. Otherwise, the behavior recognition unit 505 calculates the degree of similarity at 0. It should be noted that the degree of similarity is calculated according to a known technique and that the detailed explanation of the calculation is thus omitted.

The behavior recognition unit 505 compares the calculated degree of similarity and a specific threshold (step S105). When the degree of similarity is equal to or larger than the specific threshold (Yes in step S105), the behavior recognition unit 505 outputs the behavior label corresponding to the movement pattern data sequence having the maximum degree of similarity (step S106).

According to the behavior recognition apparatus in the fifth embodiment described thus far, when: the arm posture matches the predetermined arm posture; the grip state matches the predetermined grip state; and the time at which a velocity variation occurs is detected, only the hand movement data of the detected time at which the velocity variation occurs is selected as the hand movement data used for behavior recognition. Here, the arm posture and the grip state are used for behavior recognition as well. Therefore, the behavior recognition can be achieved with consideration given to the hand position and the object grip state in which the behavior is performed. On this account, as compared to the first embodiment, the user behavior can be recognized more accurately.

Although the behavior recognition apparatuses in the embodiments according to the present invention have been described thus far, the present invention is not limited to these embodiments.

For example, in the above embodiments, the time detected by the velocity variation detection unit 102 at which a velocity variation occurs is a time at which the hand velocity is equal to or smaller than the specific threshold. However, the present invention is not limited to this. For instance, the time to be detected may be a time at which a predetermined operation is performed. For example, when a cosine distance between a velocity vector of a certain time and a velocity vector of a time next to the certain time is below a specific threshold, this certain time may be the time at which the hand velocity variation occurs. With this, a time at which the user intentionally makes a steep change in the hand movement can be detected. As one example, suppose that the user holds out the hand parallel to the ground to reach for a glass, holds the glass, and then brings the glass up to the mouth like pulling the glass towards the user's body. In this case, when a cosine distance between a velocity vector of the hand being held out and a velocity vector of the hand pulling the glass toward the body is below a specific threshold, this indicates that the orientation of the hand movement is significantly changed. In this way, a time at which a movement sequence is interrupted, that is, a time at which an intentional movement occurs, can be detected.

Also, to be more specific, each of the above-described apparatuses may be a computer system configured by a microprocessor, a ROM, a RAM, a hard disk drive, a display unit, a keyboard, a mouse, and so forth. The RAM or the hard disk drive stores computer programs. The microprocessor operates according to the computer programs, so that the functions of the components included in the computer system are carried out. Here, note that a computer program includes a plurality of instruction codes indicating instructions to be given to the computer so as to achieve a specific function.

Moreover, some or all of the components included in each of the above-described apparatuses may be realized as a single system LSI (Large Scale Integration). The system LSI is a super multifunctional LSI manufactured by integrating a plurality of components onto a signal chip. To be more specific, the system LSI is a computer system configured by a microprocessor, a ROM, a RAM, and so forth. The RAM stores computer programs. The microprocessor operates according to the computer programs, so that the functions of the system LSI are carried out.

Furthermore, some or all of the components included in each of the above-described apparatuses may be implemented as an IC card or a standalone module that can be inserted into and removed from the corresponding apparatus. The IC card or the module is a is computer system configured by a microprocessor, a ROM, a RAM, and so forth. The IC card or the module may include the aforementioned super multifunctional LSI. The microprocessor operates according to the computer programs, so that the functions of the IC card or the module are carried out. The IC card or the module may be tamper resistant.

Also, the present invention may be the methods described above. Each of the methods may be a computer program implemented by a computer, or may be a digital signal of the computer program.

Moreover, the present invention may be the aforementioned computer program or digital signal recorded onto a computer readable recording medium, such as a flexible disk, a hard disk, a CD-ROM, an MO, a DVD, a DVD-ROM, a DVD-RAM, a BD (Blu-ray Disc (registered trademark)), and a semiconductor memory. Also, the present invention may be the digital signal recorded onto these recording medium.

Furthermore, the present invention may be the aforementioned computer program or digital signal transmitted via a telecommunication line, a wireless or wired communication line, a network represented by the Internet, and data broadcasting.

Also, the present invention may be a computer system including a microprocessor and a memory. The memory may store the aforementioned computer program and the microprocessor may operate according to the computer program.

Moreover, by transferring the recording medium having the aforementioned program or digital signal recorded thereon or by transferring the aforementioned program or digital signal via the aforementioned network or the like, the present invention may be implemented by an independent different computer system.

Furthermore, the above embodiments may be combined.

The embodiments disclosed thus far only describe examples in all respects and are not intended to limit the scope of the present invention. It is intended that the scope of the present invention not be limited by the described embodiments, but be defined by the claims set forth below. Meanings equivalent to the description of the claims and all modifications are intended for inclusion within the scope of the following claims.

The present invention is useful, for example, as: a wearable device which is capable of observing user behaviors and continuously senses the user behaviors; a life log collection device which continuously records the user behaviors; and a home healthcare electrical appliance which monitors the health of the user or the like.

REFERENCE SIGNS LIST 102, 201, 401, 501 Hand movement observation unit
102 Velocity variation detection unit
103, 203, 303, 403, 503 Feature selection unit
104, 204, 304, 404, 504 Standard behavior pattern storage unit
105, 205, 305, 405, 505 Behavior recognition unit
202 Arm posture estimation unit
301 Body posture observation unit
302 Body posture estimation unit
402 Grip detection unit
701, 702 Velocity vector
1001 to 1004 Area

The invention claimed is:

1. A behavior recognition apparatus which recognizes a user behavior from a hand movement made by a user, the behavior recognition apparatus comprising:
   a hand movement observation unit configured to detect the hand movement made by the user and output hand movement data indicating the hand movement;
   a velocity variation detection unit configured to detect a time at which a variation in velocity of a hand of the user occurs, from the hand movement data outputted from the hand movement observation unit;
   a feature selection unit configured to select the hand movement data that is outputted from the hand movement observation unit at specific times including the time detected by the velocity variation detection unit and times before and after the detected time;
   a standard behavior pattern storage unit configured to store a movement pattern data sequence represented by a hand movement data sequence, in association with the user behavior; and
   a behavior recognition unit configured to calculate a degree of similarity between the movement pattern data sequence stored in the standard behavior pattern storage unit and the hand movement data selected by the feature selection unit, and to recognize, as the user behavior, a behavior represented by the movement pattern data sequence when the degree of similarity is highest.

2. The behavior recognition apparatus according to claim 1, further comprising an arm posture estimation unit configured to estimate an arm posture of the user relative to a body of the user, from the hand movement data outputted from the hand movement observation unit,
   wherein, when the arm posture matches a predetermined arm posture and the velocity variation detection unit detects the time at which the variation in the velocity of the hand of the user occurs, the feature selection unit is configured to select the hand movement data of the specific times including the detected time at which the variation in the velocity of the hand of the user occurs and the times before and after the detected time.

3. The behavior recognition apparatus according to claim 2, further comprising
   a body posture estimation unit configured to estimate a body posture of the user,
   wherein, when: the arm posture matches the predetermined arm posture; the body posture matches a predetermined body posture; and the velocity variation detection unit detects the time at which the variation in the velocity of the hand of the user occurs, the feature selection unit is configured to select the hand movement data of the specific times including the detected time at which the variation in the velocity of the hand of the user occurs and the times before and after the detected time.

4. The behavior recognition apparatus according to claim 2,
   wherein the standard behavior pattern storage unit is configured to store, in association with the user behavior, a pair of the movement pattern data sequence represented by the hand movement data sequence and the arm posture of the time at which a hand velocity variation occurs, and the behavior recognition unit is configured to calculate a degree of similarity between: the pair; and the hand movement data selected by the feature selection unit and the arm posture estimated by the arm posture estimation unit at the time when the variation in the velocity of the hand of the user occurs, and to recognize, as the user behavior, a behavior represented by the pair when the degree of similarity is highest.

5. The behavior recognition apparatus according to claim 1, further comprising a grip detection unit configured to estimate a grip state when a hand of the user grips an object,
wherein, when the grip state matches a predetermined grip state and the velocity variation detection unit detects the time at which the variation in the velocity of the hand of the user occurs, the feature selection unit is configured to select the hand movement data of the specific times including the detected time at which the variation in the velocity of the hand of the user occurs and the times before and after the detected time.

6. The behavior recognition apparatus according to claim 5,
wherein the standard behavior pattern storage unit is configured to store, in association with the user behavior, a pair of the movement pattern data sequence represented by the hand movement data sequence and the grip state of the time at which the variation in the velocity of the hand of the user occurs, and
the behavior recognition unit is configured to calculate a degree of similarity between: the pair; and the hand movement data selected by the feature selection unit and the grip state detected by the grip state detection unit at the time when the variation in the velocity of the hand of the user occurs, and to recognize, as the user behavior, a behavior represented by the pair when the degree of similarity is highest.

7. The behavior recognition apparatus according to claim 2, further comprising a grip detection unit configured to estimate a grip state when a hand of the user grips an object,
wherein, when: the arm posture matches the predetermined arm posture; the grip state matches a predetermined grip state; and the velocity variation detection unit detects the time at which the variation in the velocity of the hand of the user occurs, the feature selection unit is configured to select the hand movement data of the specific times including the detected time at which the variation in the velocity of the hand of the user occurs and the times before and after the detected time.

8. The behavior recognition apparatus according to claim 4, further comprising a grip detection unit configured to estimate a grip state when a hand of the user grips an object,
wherein the standard behavior pattern storage unit is configured to store, in association with the user behavior, a combination of the movement pattern data sequence represented by the hand movement data sequence, the arm posture of the time at which the variation in the velocity of the hand of the user occurs, and the grip state of the time at which the variation in the velocity of the hand of the user occurs, and
the behavior recognition unit is configured to calculate a degree of similarity between: the combination; and the hand movement data selected by the feature selection unit, the arm posture estimated by the arm posture estimation unit at the time when the variation in the velocity of the hand of the user occurs, and the grip state detected by the grip detection unit at the time when the variation in the velocity of the hand of the user occurs, and to recognize, as the user behavior, a behavior represented by the combination when the degree of similarity is highest.

9. The behavior recognition apparatus according to claim 1,
wherein the velocity variation detection unit is configured to detect, from the hand movement data, a time at which a hand velocity is equal to or smaller than a predetermined threshold, as the time at which the variation in the velocity of the hand of the user occurs.

10. The behavior recognition apparatus according to claim 1,
wherein, when a cosine distance between a hand velocity vector at a given detection time and a hand velocity vector at a next detection time following the given detection time is below a predetermined threshold, the velocity variation detection unit is configured to detect, from the hand movement data, the given detection time as the time at which the variation in the velocity of the hand of the user occurs.

11. The behavior recognition apparatus according to claim 1,
wherein, when a velocity gradient difference between a hand velocity vector at a given detection time and a hand velocity vector at a next detection time following the given detection time is below a predetermined threshold, the velocity variation detection unit is configured to detect, from the hand movement data, the given detection time as the time at which the variation in the velocity of the hand of the user occurs.

12. A behavior recognition method of recognizing a user behavior from a hand movement made by a user, the behavior recognition method comprising:
detecting the hand movement made by the user and outputting hand movement data indicating the hand movement;
detecting a time at which a variation in velocity of a hand of the user occurs, from the hand movement data outputted in the detecting of a hand movement;
selecting the hand movement data that is outputted in the detecting of a hand movement at specific times including the time detected in the detecting of a time and times before and after the detected time;
a standard behavior pattern storage unit configured to store a movement pattern data sequence; and
calculating a degree of similarity between a movement pattern data sequence stored in a standard behavior pattern storage unit and the hand movement data selected, and recognizing, as the user behavior, a behavior represented by the movement pattern data sequence when the degree of similarity is highest, the movement pattern data sequence being represented by a hand movement data sequence and stored in association with the user behavior.

13. A non-transitory computer-readable recording medium storing a program for recognizing a user behavior from a hand movement made by a user for use in a computer and causing the computer to execute step comprising:
detecting the hand movement made by the user and outputting hand movement data indicating the hand movement;
detecting a time at which a variation in velocity of a hand of the user occurs, from the hand movement data outputted in the detecting of a hand movement;
selecting the hand movement data that is outputted in the detecting of a hand movement at specific times including the time detected in the detecting of a time and times before and after the detected time;

a standard behavior pattern storage unit configured to store a movement pattern data sequence; and calculating a degree of similarity between a movement pattern data sequence stored in a standard behavior pattern storage unit and the hand movement data selected, and recognizing, as the user behavior, a behavior represented by the movement pattern data sequence when the degree of similarity is highest, the movement pattern data sequence being represented by a hand movement data sequence and stored in association with the user behavior.

* * * * *